United States Patent
Kimura et al.

(10) Patent No.: US 11,291,373 B2
(45) Date of Patent: Apr. 5, 2022

(54) DEEP-BODY-TEMPERATURE ESTIMATION SYSTEM, HEAT STRESS WARNING SYSTEM, AND DEEP-BODY-TEMPERATURE ESTIMATION METHOD

(71) Applicant: TEIJIN LIMITED, Osaka (JP)

(72) Inventors: Tasuku Kimura, Osaka (JP); Hirokazu Hayashi, Osaka (JP); Ryo Yasumitsu, Osaka (JP); Hiroshi Nose, Matsumoto (JP); Yu Ogawa, Matsumoto (JP)

(73) Assignee: TEIJIN LIMITED, Osaka (JP)

( * ) Notice: Subject to any disclaimer, the term of this patent is extended or adjusted under 35 U.S.C. 154(b) by 105 days.

(21) Appl. No.: 16/635,390

(22) PCT Filed: Jun. 15, 2018

(86) PCT No.: PCT/JP2018/022899
§ 371 (c)(1),
(2) Date: Jan. 30, 2020

(87) PCT Pub. No.: WO2019/026439
PCT Pub. Date: Feb. 7, 2019

(65) Prior Publication Data
US 2020/0367758 A1 Nov. 26, 2020

(30) Foreign Application Priority Data
Jul. 31, 2017 (JP) .............................. JP2017-147355

(51) Int. Cl.
*A61B 5/01* (2006.01)
*A61B 5/00* (2006.01)

(52) U.S. Cl.
CPC .............. *A61B 5/01* (2013.01); *A61B 5/6804* (2013.01); *A61B 5/746* (2013.01);
(Continued)

(58) Field of Classification Search
CPC ... A61B 5/01; A61B 5/015; A61B 2562/0219; A61B 2562/0247; A61B 2562/0271
See application file for complete search history.

(56) References Cited

U.S. PATENT DOCUMENTS

| 2012/0068848 A1 | 3/2012 | Campbell et al. |
| 2015/0057963 A1 | 2/2015 | Zakharov et al. |

FOREIGN PATENT DOCUMENTS

| JP | 2004-030180 A | 1/2004 |
| JP | 2008220517 A * | 9/2008 |

(Continued)

OTHER PUBLICATIONS

R. Indu Shekar, T. M. Kotresh, P. M. Damodhara Rao, M. N. Satheesh Kumar, Siddaramaiah, Md. S. Rahman. "Flammability behavior of fiber-fiber hybrid fabrics and composites". Jun. 16, 2011. Journal of Applied Polymer Science. vol. 122. Issue 4. 2295-2301 (Year: 2011).*

(Continued)

*Primary Examiner* — Patrick Fernandes
*Assistant Examiner* — Severo Antonio P Lopez
(74) *Attorney, Agent, or Firm* — Sughrue Mion, PLLC

(57) ABSTRACT

A temperature sensor (210) measures a temperature inside clothes being a temperature inside the clothes worn by a user. The acceleration sensor (220) detects acceleration applied to the user. A processing device (100) estimates a deep body temperature that is a temperature inside the body of the user based on the temperature inside the clothes measured by the temperature sensor (210) and an acceleration detected by the acceleration sensor (220).

13 Claims, 16 Drawing Sheets

(52) U.S. Cl.
CPC .......... *A61B 2562/0219* (2013.01); *A61B 2562/0247* (2013.01); *A61B 2562/0271* (2013.01)

(56) References Cited

FOREIGN PATENT DOCUMENTS

| WO | WO-2017183495 A1 * | 10/2017 | .......... D03D 15/513 |
| WO | WO-2017213011 A1 * | 12/2017 | .............. A61B 5/01 |

OTHER PUBLICATIONS

N Nishihara, S Tanabe, H Hayama, M Komatsu. "A Cooling Vest for Working Comfortably in a Moderately Hot Environment". 2002. Journal of Physiological Anthropology and Applied Human Science. 2002. vol. 21. Issue 1. 75-82 (Year: 2002).*

Enomoto M, Suehiro K, Muraoka Y, Inoue K, Sumita M. "Physical Properties of Polyurethane Blend Dope-Coated Fabrics". Aug. 1, 1997. Textile Research Journal. vol. 67. Issue 8. 601-608 (Year: 1997).*

Ishimaru S. "Heat-Controllable Man-Made Fibers". Aug. 17, 2016. The Society of Fiber Science and Techno J. (eds) High-Performance and Specialty Fibers. 261-269 (Year: 2016).*

Supplementary Partial European Search Report dated May 28, 2021 from the European Patent Office in EP Application No. 18841143.3.

Takashi Hamatani et al., "Proposal of deep body temperature estimation method based on bio-thermal model using wearable sensor", Research report of Information Processing Society of Japan, Intelligent Transport Systems and Smart Community (ITS) 2014-ITS-059 [online], Nov. 20, 2014, pp. 1-5.

Takashi Hamatani et al., "A Study on Deep Body Temperature Estimation Using Wearable Sensor", Research report of Information Processing Society of Japan, Mobile Computing and Ubiquitous Communications (MBL), 2014-MBL-072 [online], Aug. 27, 2014, pp. 1-5.

Takashi Hamatani et al., "A Solar Radiation Model and Parameter Calibration in a Human Thermal Model Using a Wearable Sensor", Proceedings of Multimedia, Distributed, Cooperative, and Mobile Symposium (DICOMO2015), Information Processing Society of Japan Symposium Series, [CD-ROM], Jul. 2015, pp. 381-391 (11 pages), vol. 2015, No. 1.

International Search Report for PCT/JP2018/022899 dated Aug. 21, 2018 [PCT/ISA/210].

* cited by examiner

FIG. 6

MASTER DATA OF SUBJECT

| SUBJECT | AGE | SEX | HEIGHT (cm) | WEIGHT (kg) | BMI | BODY SURFACE AREA (cm²) | MEASUREMENT TIME (min) | WEIGHT AFTER EXERCISE (kg) | WEIGHT DIFFERENCE (kg) |
|---|---|---|---|---|---|---|---|---|---|
| S | 25 | Male | 170 | 52.78 | 18.3 | 15564 | 30 | 52.19 | 0.59 |
| H | 29 | Male | 177 | 55.29 | 17.6 | 16319 | 32 | 55.19 | 0.10 |
| M | 28 | Male | 174 | 67.78 | 22.4 | 17663 | 35 | 67.13 | 0.65 |
| Y | 23 | Male | 172 | 81.48 | 27.5 | 19020 | 35 | 80.89 | 0.59 |
| K | 26 | Male | 168 | 63.5 | 22.5 | 16764 | 34 | 63.25 | 0.25 |
| U | 37 | Male | 170 | 64.99 | 22.5 | 17071 | 33 | 65 | −0.01 |

FIG. 7

RESULT DATA OF EXAMPLE 1
(SEPARATELY CALCULATE EVERY PARAMETER)

| SUBJECT | C1 | C2 | R1 | R2 | SLOPE | CORRELATION COEFFICIENT | INTERCEPT |
|---|---|---|---|---|---|---|---|
| S | 19 | 19 | 2.1 | 25 | 1.016 | 0.994 | 0.014 |
| H | 21 | 23 | 2.5 | 25 | 1.069 | 0.969 | −0.027 |
| M | 23 | 23 | 2.5 | 25 | 0.954 | 0.989 | −0.021 |
| Y | 23 | 23 | 2.5 | 25 | 0.882 | 0.977 | 0.168 |
| K | 20 | 21 | 2.5 | 20 | 0.975 | 0.996 | 0.016 |
| U | 20 | 21 | 2 | 25 | 1.082 | 0.974 | −0.032 |
| AVG | 21.0 | 21.9 | 2.4 | 24.3 | 1.007 | 0.981 | 0.013 |
| SD | 1.53 | 1.57 | 0.22 | 1.89 | 0.074 | 0.011 | 0.071 |
| SE | 0.58 | 0.59 | 0.08 | 0.71 | 0.028 | 0.004 | 0.027 |

RELATION BETWEEN ACTUAL MEASURED VALUE AND CALCULATED VALUE

FIG. 9

RESULT DATA OF EXAMPLE 2
(USE AVERAGE VALUE TO EVERY PARAMETER)

| SUBJECT | C1 | C2 | R1 | R2 | SLOPE | CORRELATION COEFFICIENT | INTERCEPT |
|---|---|---|---|---|---|---|---|
| S | 21.6 | 22.4 | 2.37 | 24.3 | 1.511 | 0.994 | 0.012 |
| H | 21.6 | 22.4 | 2.37 | 24.3 | 1.023 | 0.969 | −0.028 |
| M | 21.6 | 22.4 | 2.37 | 24.3 | 0.837 | 0.989 | −0.021 |
| Y | 21.6 | 22.4 | 2.37 | 24.3 | 0.720 | 0.978 | 0.167 |
| K | 21.6 | 22.4 | 2.37 | 24.3 | 1.086 | 0.996 | 0.018 |
| U | 21.6 | 22.4 | 2.37 | 24.3 | 1.436 | 0.973 | −0.031 |
| AVG | – | – | – | – | 1.102 | 0.983 | 0.019 |
| SD | – | – | – | – | 0.316 | 0.011 | 0.075 |
| SE | – | – | – | – | 0.129 | 0.005 | 0.031 |

FIG. 10

RESULT DATA 1 OF EXAMPLE 3
(FOCUS ON WEIGHT FOR EVERY PARAMETER)

| SUBJECT | WEIGHT (kg) | C1 | C2 | R1 | R2 | C1*R1 | C2*R2 |
|---|---|---|---|---|---|---|---|
| S | 52.78 | 19 | 19 | 2.1 | 25 | 39.9 | 475 |
| H | 55.29 | 21 | 23 | 2.5 | 25 | 52.5 | 575 |
| M | 67.78 | 23 | 23 | 2.5 | 25 | 57.5 | 575 |
| Y | 81.48 | 23 | 23 | 2.5 | 25 | 57.5 | 575 |
| K | 63.5 | 20 | 21 | 2.5 | 20 | 50.0 | 420 |
| U | 64.99 | 20 | 21 | 2.0 | 25 | 40.0 | 525 |
| CORRELATION COEFFICIENT | | 0.754 | 0.555 | 0.356 | 0.039 | 0.592 | 0.375 |
| $r^2$ | | 0.568 | 0.308 | 0.127 | 0.001 | 0.35 | 0.141 |

FIG. 12

RESULT DATA 2 OF EXAMPLE 3
(CALCULATE C1 AND C2 FROM WEIGHT)

| SUBJECT | WEIGHT (kg) | C1 | C2 | R1 | R2 | C1*R1 | C2*R2 | CORRELATION COEFFICIENT | SLOPE |
|---|---|---|---|---|---|---|---|---|---|
| S | 52.78 | 19.6 | 20.6 | 2.4 | 24.2 | 41.1 | 516.1 | 0.994 | 1.313 |
| H | 55.29 | 19.9 | 20.9 | 2.4 | 24.2 | 49.7 | 521.7 | 0.969 | 0.921 |
| M | 67.78 | 21.4 | 22.0 | 2.4 | 24.2 | 53.6 | 549.4 | 0.989 | 0.852 |
| Y | 81.48 | 23.1 | 23.2 | 2.4 | 24.2 | 57.8 | 579.8 | 0.977 | 0.894 |
| K | 63.5 | 20.9 | 21.6 | 2.4 | 24.2 | 52.2 | 431.9 | 0.996 | 1.046 |
| U | 64.99 | 21.1 | 21.7 | 2.4 | 24.2 | 42.2 | 543.2 | 0.974 | 1.182 |
| AVG | | 21.0 | 21.7 | ~ | ~ | 49.4 | 523.7 | 0.98 | 1.080 |
| SD | | 1.26 | 0.91 | ~ | ~ | 6.6 | 50.3 | 0.011 | 0.237 |
| SE | | 0.51 | 0.37 | ~ | ~ | 2.7 | 20.5 | 0.005 | 0.097 |

FIG. 13

RESULT DATA 1 OF EXAMPLE 4
(FOCUS ON BODY SURFACE AREA FOR EVERY PARAMETER)

| SUBJECT | BODY SURFACE AREA ($cm^2$) | C1 | C2 | R1 | R2 | C1*R1 | C2*R2 |
|---|---|---|---|---|---|---|---|
| S | 15564 | 19 | 19 | 2.1 | 25 | 39.9 | 475 |
| H | 16319 | 21 | 23 | 2.5 | 25 | 52.5 | 575 |
| M | 17663 | 23 | 23 | 2.5 | 25 | 57.5 | 575 |
| Y | 19020 | 23 | 23 | 2.5 | 25 | 57.5 | 575 |
| K | 16764 | 20 | 21 | 2.5 | 20 | 50.0 | 420 |
| U | 17071 | 20 | 21 | 2.0 | 25 | 40.0 | 525 |
| CORRELATION COEFFICIENT | | 0.844 | 0.680 | 0.429 | 0.125 | 0.681 | 0.511 |
| $r^2$ | | 0.712 | 0.463 | 0.184 | 0.016 | 0.464 | 0.261 |

FIG. 14

RESULT DATA 2 OF EXAMPLE 4
(CALCULATE C1 AND C2 FROM BODY SURFACE AREA)

| SUBJECT | BODY SURFACE AREA (cm²) | C1 | C2 | R1 | R2 | C1*R1 | C2*R2 | CORRELATION COEFFICIENT | SLOPE |
|---|---|---|---|---|---|---|---|---|---|
| S | 15564 | 16.3 | 19.7 | 2.4 | 24.2 | 34.2 | 493.6 | 0.994 | 1.044 |
| H | 16319 | 17.1 | 20.4 | 2.4 | 24.2 | 42.7 | 510.6 | 0.969 | 0.783 |
| M | 17663 | 18.4 | 21.6 | 2.4 | 24.2 | 46.0 | 540.8 | 0.989 | 0.729 |
| Y | 19020 | 19.8 | 22.9 | 2.4 | 24.2 | 49.4 | 571.4 | 0.978 | 0.755 |
| K | 16764 | 17.5 | 20.8 | 2.4 | 24.2 | 43.8 | 416.5 | 0.996 | 0.861 |
| U | 17071 | 17.8 | 21.1 | 2.4 | 24.2 | 35.6 | 527.5 | 0.974 | 0.947 |
| AVG | | 17.8 | 21.1 | – | – | 42.0 | 510.1 | 0.98 | 0.85 |
| SD | | 1.19 | 1.07 | – | – | 5.9 | 53.0 | 0.011 | 0.123 |
| SE | | 0.49 | 0.44 | – | – | 2.4 | 21.6 | 0.005 | 0.050 |

FIG. 15

RESULT DATA OF EXAMPLE 5
(CALCULATE C1 FROM WEIGHT,
CALCULATE C2 FROM BODY SURFACE AREA)

| SUBJECT | WEIGHT (kg) | C1 | C2 | R1 | R2 | CORRELATION COEFFICIENT | SLOPE | INTERCEPT | T VALUE | P VALUE |
|---|---|---|---|---|---|---|---|---|---|---|
| S | 52.78 | 19.6 | 19.7 | 2.4 | 24.2 | 0.99 | 1.22 | 0.01 | 48.0 | 1.9E-28 |
| H | 55.29 | 19.9 | 20.4 | 2.4 | 24.2 | 0.97 | 0.88 | -0.03 | 21.5 | 8.5E-20 |
| M | 67.78 | 21.4 | 21.6 | 2.4 | 24.2 | 0.99 | 0.82 | -0.02 | 37.9 | 8.4E-29 |
| Y | 81.48 | 23.1 | 22.9 | 2.4 | 24.2 | 0.98 | 0.86 | 0.17 | 26.6 | 6.9E-24 |
| K | 63.50 | 20.9 | 20.8 | 2.4 | 24.2 | 1.00 | 0.99 | 0.02 | 59.7 | 2.2E-34 |
| U | 64.99 | 21.1 | 21.1 | 2.4 | 24.2 | 0.97 | 1.34 | -0.03 | 23.6 | 2.2E-21 |
| AVG | | 21.0 | 21.1 | - | - | 0.98 | 1.02 | 0.02 | - | - |
| SD | | 1.261 | 1.071 | - | - | 0.011 | 0.216 | 0.075 | - | - |
| SE | | 0.515 | 0.437 | - | - | 0.005 | 0.088 | 0.031 | - | - |

FIG. 16

FINAL RESULT DATA OF EXAMPLE

| | | C1:WEIGHT C2:BODY SURFACE AREA | C1:WEIGHT C2:AVG | C1:WEIGHT C2:WEIGHT | C1:BODY SURFACE AREA C2:BODY SURFACE AREA |
|---|---|---|---|---|---|
| CORRELATION COEFFICIENT | AVG | 0.98 | 0.98 | 0.98 | 0.98 |
| | SD | 0.011 | 0.011 | 0.011 | 0.011 |
| | SE | 0.005 | 0.005 | 0.005 | 0.005 |
| SLOPE | AVG | 1.02 | 1.02 | 1.05 | 0.86 |
| | SD | 0.216 | 0.245 | 0.231 | 0.170 |
| | SE | 0.088 | 0.100 | 0.094 | 0.069 |
| Intercept | AVG | 0.02 | 0.02 | 0.02 | 0.02 |
| | SD | 0.075 | 0.075 | 0.075 | 0.074 |
| | SE | 0.031 | 0.031 | 0.031 | 0.030 |

DEEP-BODY-TEMPERATURE ESTIMATION SYSTEM, HEAT STRESS WARNING SYSTEM, AND DEEP-BODY-TEMPERATURE ESTIMATION METHOD

CROSS REFERENCE TO RELATED APPLICATIONS

This application is a National Stage of International Application No. PCT/JP2018/022899 filed Jun. 15, 2018, claiming priority based on Japanese Patent Application No. 2017-147355, filed on Jul. 31, 2017.

TECHNICAL FIELD

The present disclosure relates to a deep-body-temperature estimation system, a heat-stress alarm system, and a deep-body-temperature estimation method.

BACKGROUND ART

Prevention of a user who performs fire extinguishing activities as a fireman or a user who works under the blazing sun firm suffering heatstroke is important. For example, a method of detecting the heat stress that causes heatstroke and generating an alarm depending on the result of the detection result is conceived for preventing heatstroke.

For example, Patent Literature 1 discloses a technique to ascertain heat stress condition based on the inner temperature of protective equipment as detected by a temperature sensor. The technique disclosed in Patent Literature 1 detects the inner temperature of the protective equipment based on a temperature sensor, based on an assumption that heatstroke can be predicted by ascertaining the inner temperature of the protective equipment.

CITATION LIST

Patent Literature

Patent Literature 1: Unexamined Japanese Patent Application Kokai Publication No. 2004-30180

SUMMARY OF INVENTION

Technical Problem

A relationship is known to exist between heatstroke and the deep body temperature. That is, the deep body temperature can be an index indicating danger of heat stress, such as heatstroke, that a human body feels. However, previously existing technology does not directly predict the deep body temperature, and thereby prediction accuracy of heatstroke is insufficient. In addition, a temperature measuring probe needs to be inserted into the human body via the mouth, ear, or anus in order to measure the deep body temperature. Thus, the measurement of the deep body temperature is difficult to perform when the user is in the middle of work.

In order to solve the aforementioned shortcoming, an objective of the present disclosure is to provide a deep-body-temperature estimation system that enable estimation of the deep body temperature of the user with high accuracy, a heat-stress alarm system, and a deep-body-temperature estimating method.

Solution to Problem

In order to attain the aforementioned objective, a deep-body-temperature estimation system according to the first aspect of the present disclosure includes, a temperature sensor configured to measure a temperature inside clothes being a temperature inside the clothes worn by a user; and an acceleration sensor configured to detect an acceleration applied to the user, wherein the deep-body-temperature estimation system estimates a deep body temperature that is a temperature inside a body of the user.

The deep-body-temperature estimation system may further include deep-body-temperature estimation means for estimating the deep body temperature based on the temperature inside the clothes measured by the temperature sensor and the acceleration detected by the acceleration sensor.

The deep-body-temperature estimation system may includes heat production amount estimation means for estimating a heat production amount generated inside the body of the user based on the acceleration detected by the acceleration sensor, wherein the deep-body-temperature estimation means estimates the deep body temperature based on the temperature inside clothes measured by the temperature sensor and the heat production amount estimated by the heat production amount estimation means.

The deep-body-temperature estimation means may estimate the deep body temperature by using a mathematical model indicating a correspondence relation among the temperature inside the clothes, the heat production amount, and the deep body temperature.

The mathematical model may be expressed by a simultaneous differential equation including a first equation where an amount of change in a first heat amount is expressed by a difference between the heat production amount and a first heat flow amount that is a heat flow amount supplied from muscles of the user to the blood of the user, the amount of change in the first heat amount being an heat amount of the muscles of the user, a second equation where an amount of change in the second heat amount is expressed by a difference between the first heat flow amount and a second heat flow amount that is a heat flow amount supplied from the blood of the user to an inside of the clothes, the amount of change in the second heat amount being a heat amount of the blood of the user, a third equation where the first heat flow amount is expressed by an ratio of a difference between an amount of change in the first temperature that is a temperature of the muscles of the user and the amount of change in the second temperature that is the temperature of the blood of the user to a first thermal resistance value that is a thermal resistance value from the muscle of the user to the blood of the user, a fourth equation wherein the second heat flow amount is expressed by an ratio of a difference between the amount of change of the second temperature and the amount of change in the temperature inside the clothes to a second thermal resistance value that is a thermal resistance value from the blood of the user to the inside of the clothes, a fifth equation where the amount of change in the first temperature is expressed by a ratio of the first heat amount to a first heat capacity that is a heat capacity of the muscles of the user, and a sixth equation where an amount of change in the second temperature is expressed by a ratio of the second heat amount to a second heat capacity that is a heat capacity of the blood of the user, and the deep-body-temperature estimation means estimates the second temperature as the deep body temperature.

The first heat capacity and the second heat capacity may be values obtained based on physical features of the user, and the first thermal resistance value and the second thermal resistance value are predetermined values.

The deep-body-temperature estimation system may further include an air pressure sensor configured to detect an air pressure around the user, wherein the heat production amount estimation means estimates the heat production amount based on the acceleration detected by the acceleration sensor and the air pressure detected by the air pressure sensor.

The deep-body-temperature estimation system may further include an angular rate sensor configured to detect an angular rate applied to the user; and a magnetic sensor configured to detect a direction of a magnetic field around the user, wherein the acceleration sensor, the angular rate sensor, and the magnetic sensor may be fixed to one another, and the heat production amount estimation means may estimate the heat production amount based on the acceleration detected by the acceleration sensor, the angular rate detected by the angular rate sensor, and the direction detected by the magnetic sensor.

The deep-body-temperature estimation system may further include notification means configured to provide notification of an abnormality of the user based on the deep body temperature estimated by the deep-body-temperature estimation means.

The clothes may have heat shielding effect.

The heat shielding effect may satisfy a requirement in which the HTI 24 that is measured by the method defined in ISO 9151 is three seconds or more.

The clothes may have an air permeability of 1.0 $cm^3/cm^2/s$ or below measured by a method that is defined in JIS L 1096 and uses a fragile type tester.

The clothes may have a moisture permeability of 1000 $g/m^2/h$ or below measured by a method that is defined in JIS L 1099 and uses a cup method.

The clothes may have a thermal conductivity of 1 kcal/h/m/° C. or below.

In order to attain the aforementioned objective, a heat-stress alarm system according to the second aspect of the present disclosure includes, deep-body-temperature estimation means configured to estimate a deep body temperature that is a temperature inside a body of a user based on a temperature inside clothes that is a temperature inside the clothes worn by the user and an acceleration applied to the user, and alarming means configured to generate an alarm based on the deep body temperature estimated by the deep-body-temperature estimation means.

In order to attain the aforementioned objective, deep-body-temperature estimation method according to the third aspect of the present disclosure includes, measuring a temperature inside clothes that is a temperature inside the clothes worn by a user;

detecting acceleration applied to the user; and estimating a deep body temperature that is a temperature inside a body of the user based on the measured temperature inside the clothes and the detected acceleration.

Advantageous Effects of Invention

The present disclosure enables estimation of a deep body temperature of the user with high accuracy.

BRIEF DESCRIPTION OF DRAWINGS

FIG. 6 is a diagram of basic data of a subject;

FIG. 7 is a diagram of result data of Example 1;

FIG. 9 is a diagram of result data of Example 2;

FIG. 10 is a diagram of result data 1 of Example 3;

FIG. 12 is a diagram of result data 2 of Example 3;

FIG. 13 is a diagram of result data 1 of Example 4;

FIG. 14 is a diagram of result data 2 of Example 4;

FIG. 15 is a diagram of result data of Example 5; and

FIG. 16 is a diagram of the final result data of the examples.

DESCRIPTION OF EMBODIMENTS

Embodiments of the present disclosure are described below with reference to the drawings. Throughout the drawings, components that are the same or equivalent are assigned the same reference signs.

Embodiments

Figure 1:
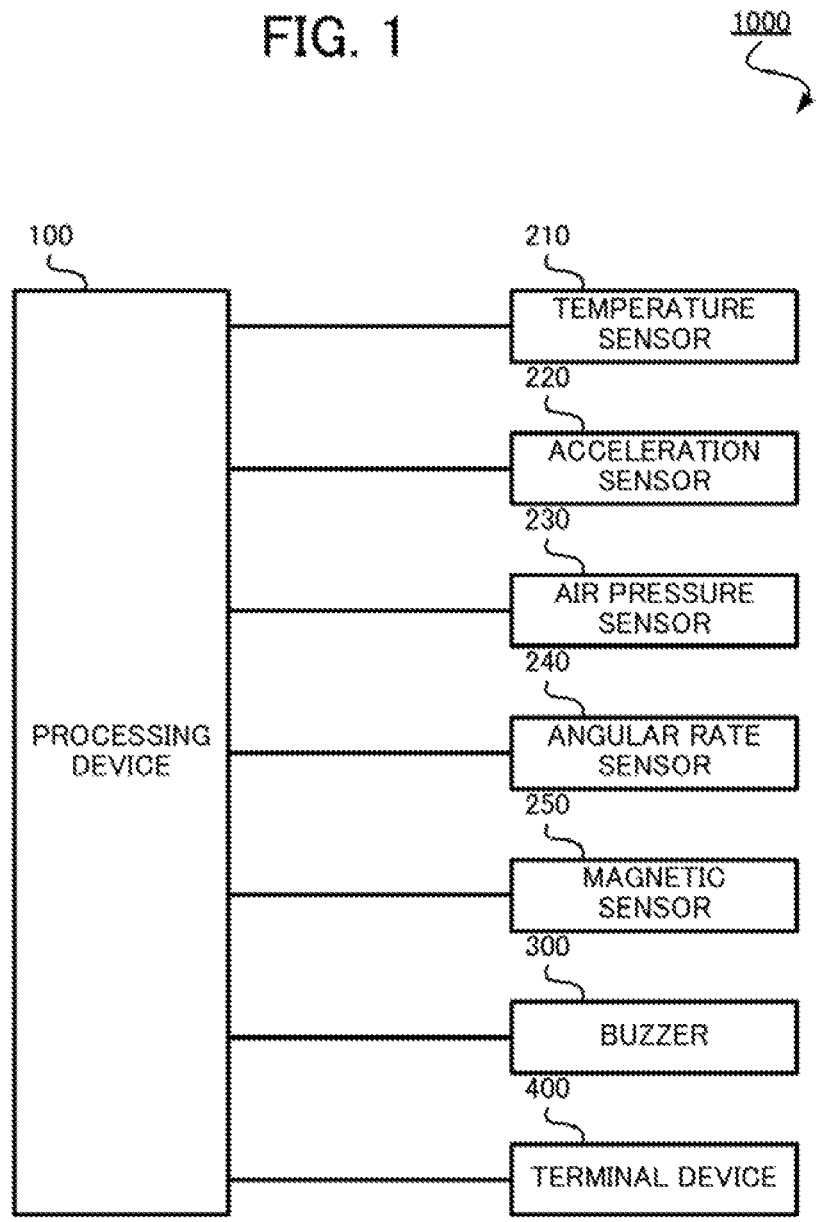
FIG. 1 is a configuration diagram of a deep-body-temperature estimation system according to an embodiment of the present disclosure.

FIG. 1 is a configuration diagram of a deep-body-temperature estimation system 1000 according to an embodiment of the present disclosure. The deep-body-temperature estimation system 1000 is a system that estimates a body temperature of the core part of the body of the user, referred to hereinafter as the "deep body temperature". More specifically, the deep-body-temperature estimation system 1000 is a system that estimates the deep body temperature of the user using a mathematical model based on the heat generated by the motion of the user (hereinafter referred to as "heat production amount") and the temperature of a space between the user and clothes worn by the user (hereinafter referred to as "temperature inside clothes").

In addition, the deep-body-temperature estimation system 1000 has, in addition to the function of estimating the deep body temperature a function of generating an alarm when there is a risk of heatstroke based on the deep body temperature. In the present embodiment, the "user" relets to a firefighter who performs firefighting activities and wears a fire-proof suit as the clothes. Note that the user, rather than a firefighter, may be a worker who works under the blazing sun. Furthermore, the clothes worn by the user are not limited to the fire-proof suit. The clothes worn by the user are preferably clothes with a heat shielding effect higher than that of general clothes.

An example of the heat shielding property referred herein as an index of the heat shielding effect is, without particular limitation, the property of a fabric or the like used in the clothes having a time required for the temperature to elevate and reach 24° C. (HTI 24) after exposure to a predetermined flame that is three seconds or more as measured by the method defined in ISO 9151.

Such clothes with a high heat shielding effect are, for example, those including a multi-layer fabric described in Unexamined Japanese Patent Application Kokai Publication No. 2014-091307 and Unexamined Japanese Patent Application Kokai Publication No. 2011-106069. That is, the clothes preferably include a layered fabric with at least two layers, an outer layer and an inner layer. The thickness of each layer of the layered fabric greatly affects the heat shielding property. For this reason, as described, for example, in Unexamined Japanese Patent Application Kokai Publication No. 2010-255124, the clothes preferably use a fabric having the thickness of the outer surface layer and the thickness of the inner layer satisfying the equation below, without particular limitation.

$$5.0 \text{ mm} \geq \text{thickness of heat shielding layer (mm)} \geq -29.6 \times (\text{thickness of outer surface layer (mm)}) + 14.1 \text{ (mm)}$$

In the multi-layer fabric, the fabric form may change from the normal state thereof upon exposure to flames. For example, the fabric thickness may conceivably increase upon exposure to the flames. In addition, regarding the heat shielding property of the fabric that is included in the clothes, an HTI 24 measured by the method defined in ISO 9151 is preferably three seconds or more. HTI 24 is the time for the temperature to elevate and reach 24° C. upon exposure to the flames.

The multi-layer fabric is preferably made of a fiber material having high flame retardancy for protection of the temperature sensor. For example, the limiting oxygen index (LOI) of the fiber constituting the multi-layer fabric is 21 or more, and preferably 24 or more. The limiting oxygen index is the oxygen concentration (%) of the atmosphere required to continue combustion, and an LOI of 21 or more means that self-extinguishing occurs and combustion does not continue in normal air, and thus the fabric can exhibits high heat resistance. In this regard, the limiting oxygen index (LOI) is the value measured by JIS L 1091 (method E).

In this way, high heat resistance can be obtained by using fibers having the limiting oxygen index (LOI) of 21 or more in the outermost layer. The above-mentioned fibers include meta-aramid fibers, para-aramid fibers, polybenzimidazole fibers, polyimide fibers, polyamideimide fibers, polyetherimide fibers, polyarylate fibers, polyparaphenylene benzobisoxazole fibers, novoloid fibers, polychlol fibers, flame retardant acrylic fibers, flame retardant rayon fibers, flame retardant polyester fibers, flame retardant cotton fibers, and flame retardant wool fibers.

In particular, fibers that are useful include meta-aramid fibers such as polymetaphenylene isophthalamide, para-aramid fibers such as polyparaphenylene terephthalamide with the goal of improving the strength of the woven or knitted fabric, and fibers obtained by copolymerizing the aforementioned meta-aramid fibers or para-aramid fibers with a third component. Examples of the polyparaphenylene terephthalamide copolymer include co-poly-(paraphenylene/3,4'-oxydiphenylene terephthalamide). However, flammable materials such as polyester fibers, polyamide fibers, nylon fibers, and acrylic fibers may be used in combination with the aforementioned fibers as long as flame retardancy is not impaired. Further, the fibers May be raw fibers or post-dye fibers. Further, the woven fabric may be subjected to flame-retarding processing, as may be required.

For the above-mentioned fibers, long fibers or short fibers may be used. Further, two or more kinds of the aforementioned fibers may be mixed or blended. In particular, in accordance with the present disclosure, as the fabric used for the outer layer, the meta-aramid fibers and the para-aramid fibers are preferably used in the form of filaments or blended spun yarns. The spun yarn used may be single ply or double ply. The mixing ratio of the para-aramid fibers is preferably 5% by weight or more based on total weight of the fibers constituting the fabric. Since the para-aramid fibers are prone to fibrillation, the mixing ratio of the para-aramid fibers is preferably 60% by weight or below based on total weight of the fibers constituting the fabric.

The above fabric may be used in the form of a woven fabric, knitted fabric, nonwoven fabric or the like, but is preferably as woven fabric. In addition, for the woven fabric, any woven structure such as plain weave, twill weave, satin weave or the like may be used. In the case of the woven fabric and knitted fabric, two kinds of fibers may be interweaved and interknitted. The fabric used for the outermost layer (i.e., the outer surface layer) preferably has a fabric weight of 140 to 500 g/m$^2$, more preferably 160 to 400 g/m$^2$, and still more preferably 200 to 400 g/m$^2$. If the fabric weight is less than 140 g/m$^2$, sufficient heat resistance may possibly not be obtained. However, if the fabric weight exceeds 500 g/m$^2$, the feeling of wear as the heat shielding activity garment may possibly be impaired.

In the multi-layer fabric, the inner layer preferably has a tensile modulus of 80 to 800 cN/dtex, a fabric thermal conductivity of 6.0 W·m$^{-1}$·k$^{-1}$ or below, preferably 5.0 W·m$^{-1}$·k$^{-1}$ or below and a specific gravity of 3.0 g/cm$^3$ or below. The transmittance of an electromagnetic wave with a wavelength of 800 to 3000 nm is preferably 10% or below, and the fabric weight is preferably 60 to 500 g/m$^2$.

The tensile elastic modulus of the fiber is preferably 80 to 800 cN/dtex, more preferably is 80 to 500 cN/dtex, and further preferably 120 to 500 cN/dtex. If the heat shielding activity garment or the like is formed of the fibers with the tensile elastic modulus of less than 80 cN/dtex, depending on the movement and posture of the wearer, the fibers sometimes elongate at some locations and the fabric becomes thin at the some locations, thereby failing to exert sufficient heat shielding effect. Further, the use of the fibers with the tensile elastic modulus exceeding 800 cN/dtex may have negative effect on the "stretch" of the resulting heat shielding activity garment or the like. Although this may be avoided by use of the spun yarn, the tensile elastic modulus is preferably 800 cN/dtex or below for attaining a sufficient effect.

In the multi-layer fabric, the fabric weight of the fabric is preferably 60 to 500 g/m$^2$, more preferably is 80 to 400 g/m$^2$, and still more preferably is 100 to 350 g/m$^2$. If the fabric weight is lower than 60 g/m$^2$, the transmission of electromagnetic waves may not be sufficiently prevented in some cases. On the other hand, if the fabric weight is higher than 500 g/m$^2$, the tendency to accumulate heat becomes conspicuous and thus there is a possibility that the heat shielding property is impaired. Also, lightweightness may possibly be impaired.

No particular limitation is imposed on the fibers which constitute the above multi-layer fabric. In order to improve the absorption and reflection of electromagnetic waves, metal, carbon, or the like can be intermixed with the fibers or adhered to the surface of the fibers. While the carbon fibers may be used as the above fibers, the fibers formed of organic polymers, which are hereinafter referred to as organic polymer fibers, may be preferably used, including aramid fibers, polybenzimidazole fibers, polyimide fibers, polyamideimide fibers, polyetherimide fibers, polyarylate fibers, polyparaphenylene benzobisoxazole fibers, novoloid fibers, polychlor fibers, flame retardant acrylic fibers, flame retardant rayon fibers, flame retardant polyester fibers, flame retardant cotton fibers, and flame retardant wool fibers.

In order to improve the electromagnetic wave absorption and the thermal conductivity of the multi-layer fabric, fine particles of carbon, gold, silver, copper, aluminum or the like can be contained in the organic polymer fibers or adhered to the surfaces of the organic polymer fibers. In this case, carbon or the like may be contained in the organic polymer fibers or imparted to the surface of the organic polymer fibers as a pigment or paint containing the carbon or the like. The ratio of the contained or adhered fine particles to a total weight of the organic polymer fibers is preferably from 0.05 to 60% by weight, and more preferably is from 0.05 to 40% by weight, although such a ratio depends on the specific gravity of the fine particles. In addition, in the case of carbon fine particles, the ratio is preferably 0.05% by weight or more, more preferably is 0.05 to 10% by weight, and further preferably is 0.05% by weight or more to less than 5% by weight. Further, in the case of aluminum fine particles, the ratio is preferably 1% by weight or more, more preferably is 1 to 20% by weight, and further preferably is 1 to 10% by weight.

The number average particle diameter of the fine particles is preferably 10 µm or below (more preferably 0.01 to 1 µm). If the carbon fiber, the metal fiber or the like itself satisfies the above requirements such as LOI value and thermal conductivity, use is possible as is without kneading fine particles therein. Examples of the fabric include, as the fabric included in the inner layer, the fabric with the content of carbon fiber or metal fiber of preferably 50% by weight or more, more preferably 80% by weight or more, and further preferably 100%.

The multi-layer fabric can include, between the above outer layer and inner layer, an intermediate layer having a moisture permeable and waterproof film laminated and bonded to the fabric which is formed of the fibers having an LOI value of 25 or more. With this configuration, the permeation of water from the outside can be suppressed while maintaining the comfort of the fabric structure. Accordingly, the above fabric structure is more suitable as the protective suit for a firefighter who performs firefighting activities such as water spraying. The fabric weight of the intermediate layer used is preferably in the range of 50 to 200 g/m². If the fabric weight is less than 50 g/m², sufficient heat shielding performance may possibly not be obtained. On the other hand, if the fabric weight is greater than 200 g/m², the weight of the heat shielding activity suit may possibly be too heavy for the water and performance may be impaired.

The fabric is preferably laminated with a thin film that is formed from polytetrafluoroethylene or the like having moisture permeation and waterproof properties, thereby improving the moisture permeation and waterproofness as well as the chemical resistance, enabling promotion of the evaporation of sweat of the wearer, and thus enabling reduction in the heat stress of the wearer. The total weight per unit area of the thin film that is used to laminate the intermediate layer is preferably in the range of 10 to 50 g/m². Even when the thin film is used to laminate the fabric of the intermediate layer, as described above, the fabric weight of the processed intermediate layer is preferably in the range of 50 to 200 g/m² as described above.

In addition, in the present embodiment, cloth having low air permeability is preferably used. The value measured by the method defined in JIS L 1096 (fragile type tester) is preferably 1.0 cm³/cm²/s or below, and is more preferably 0.01 cm³/cm²/s or below.

Furthermore, in the present embodiment, cloth having low moisture permeability is preferably used. The value measured by the method defined in JIS L 1099 (cup method) is preferably 1000 g/m²/h or below, and is more preferably 10 g/m²/h or below.

In the present embodiment, cloth having low thermal conductivity is preferably used. The thermal conductivity is preferably 1 kcal/h/m/° C. or below, and is more preferably 1 cal/h/m/° C. or below.

As illustrated in FIG. 1, the deep-body-temperature estimation system 1000 includes a processing device 100, a temperature sensor 210, an acceleration sensor 220, an air pressure sensor 230, an angular rate sensor 240, a magnetic sensor 250, a buzzer 300, and a terminal device 400. The processing device 100 and each sensor (the temperature sensor 210, the acceleration sensor 220, the air pressure sensor 230, the angular rate sensor 240, and the magnetic sensor 250) are connected to each other. In addition, the processing device 100 and the buzzer 300 are connected to each other and the processing device 100 and terminal device 400 are connected to each other via a non-illustrated network.

The processing device 100 is a module forming the heart of the deep-body-temperature estimation system 1000. The processing device 100 is, for example, a microcomputer, and a personal computer. The processing device 100 estimates, by using a predetermined mathematical model, the deep body temperature of the user based on information obtained from the sensors. In addition, upon determination that the user has high possibility of suffering heatstroke, that is, upon determination that the estimated deep body temperature is abnormal, the processing device 100 generates an alarm using light, sound, or a screen display. The processing device 100 itself may generate an alarm, or may enable the buzzer 300 or the terminal device 400 to generate an alarm. The configuration of the processing device 100 is hereinafter described with reference to FIG. 2.

Figure 2:
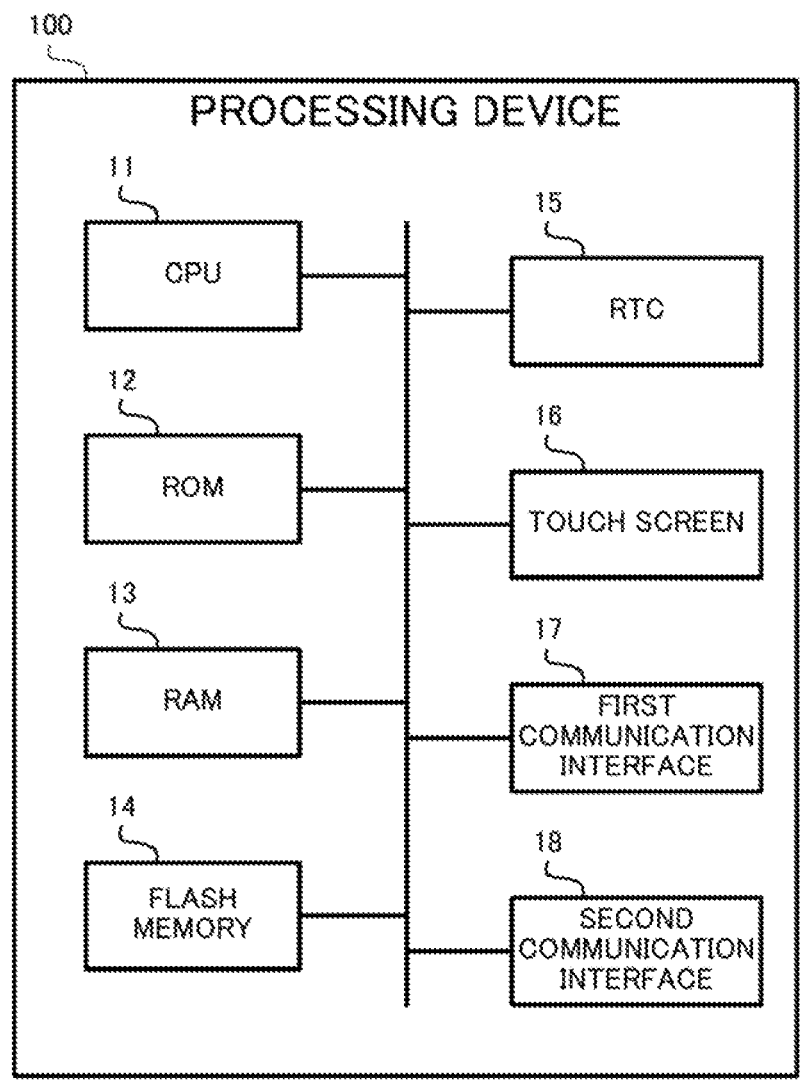
FIG. 2 is a configuration diagram of a processing device according to an embodiment of the present disclosure.

As illustrated in FIG. 2, the processing device 100 includes a central processing unit 11 (CPU), a read only memory 12 (ROM), a random access memory 13 (RAM), a flash memory 14, a real time clock 15 (RTC), a touch screen 16, a first communication interface 17, and a second communication interface 18. The components included in the processing device 100 are connected to one another via a bus.

The CPU 11 controls overall operation of the entire processing device 100. Note that the CPU 11 operates according to a program stored in the ROM 12 and uses the RAM 13 as a working area. A program and data for control of the overall operation of the processing device 100 are stored in the ROM 12. The RAM 13 is used as a working area of the CPU 11. That is, the CPU 11 temporarily writes the program and data to the RAM 13 and appropriately references the written program and data. Functions of a deep-body-temperature estimation means and heat production amount estimation means are achieved, for example, by using the CPU 11 using the RAM 13 as working area to execute the program stored in the ROM 12.

The flash memory 14 is a non-volatile memory for storage of various types of information. An RTC 15 is a device for time measurement. The RTC 15, for example, includes a battery and continues time measurement even when the power supply of the processing device 100 is turned OFF. The RTC 15 is equipped, for example, with an oscillator circuit including a quartz oscillator. The touch screen 16 detects a touch operation performed by the user and provides to the CPU 11 a signal indicating a result of the detection. Furthermore, the touch screen 16 displays an image that is based on an image signal provided from the CPU 11. The touch screen 16 in this manner functions as a user interface of the processing device 100.

The first communication interface 17 is an interface for connecting the processing device 100 to a non-illustrated network such as the Internet. The processing device 100, via the non-illustrated network, communicates with the terminal device 400. The first communication interface 17 is, for example, an interface for a wireless local area network (LAN).

The second communication interface 18 is an interface for connecting the processing device 100 to the sensors or the buzzer 300. The second communication interface 18 may be connected, via non-illustrated communication cable, to the sensors or the buzzer 300, or may be connected, via wireless communication, to the sensors or the buzzer 300. The second communication interface 18 may be an interface for a wireless LAN, or may be an interface in conformity with a universal serial bus (USB) or a recommended standard 232 (RS-232).

The temperature sensor 210 is a sensor for measuring an ambient temperature. The temperature sensor 210 is, for, example, disposed inside the clothes to measure the temperature inside the clothes. The temperature sensor 210 provides information indicating the measured temperature inside the clothes (hereinafter referred to as "temperature information") to the processing device 100. The temperature sensor 210 is, for example, a mercury type thermometer, an alcohol type thermometer, a thermistor type thermometer, an infrared type sensor, a temperature measuring sensor, and a complememyary MOS (CMOS) temperature sensor.

The acceleration sensor 220 is a sensor that measures an acceleration applied to the acceleration sensor 220. The acceleration sensor 220 is worn by the user or attached to the clothes to measure acceleration applied to the user, that is acceleration generated in the acceleration sensor 220 by the motion of the user. The acceleration sensor 220 measures the accelerations along three axes that are an X axis, a Y axis, and a Z axis. The acceleration sensor 220 provides information indicating an X-axis acceleration, a Y-axis acceleration, and a Z-axis acceleration (hereinafter referred to as "acceleration information") to the processing device 100. The acceleration sensor 220 is, for example, a semiconductor type acceleration sensor, a mechanical displacement measurement acceleration sensor, or an optical type acceleration sensor. The semiconductor type acceleration sensor is an acceleration sensor using a technology of micro electro mechanical systems (MEMS). Examples of such a semiconductor type acceleration sensor include an electrostatic capacitance type acceleration sensor, a piezoresistance type acceleration sensor, and a gas-temperature-distribution type acceleration sensor.

The air pressure sensor 230 is a sensor that measures an ambient air pressure. The air pressure sensor 230, for example, is disposed outside the clothes to measure the air pressure around the user. The air pressure sensor 230 provides information indicating the measured air pressure (hereinafter referred to as "air pressure information") to the processing device 100. The air pressure sensor 230 is, for example, an electric air pressure sensor utilizing a semiconductor, an electrostatic capacitor air pressure sensor, or a vibrating sensor.

The angular rate sensor 240 is a sensor that measures angular rate applied to the angular rate sensor 240. The angular rate sensor 240 is, for example, worn by the user or attached to the clothes, measuring the angular rate applied to the user, that is, the angular rate that is generated in the angular rate sensor 240 by the motion of the user. The angular rate sensor 240 is an acceleration sensor that measures accelerations of three axes that are the X axis, the Y axis, and the Z axis. The angular rate sensor 240 provides information indicating the measured angular rate (hereinafter referred to as "angular rate information") to the processing device 100. The angular rate sensor 240 is, for example, a gyro sensor that outputs as an electrical signal a distortion generated by Coriolis force by using a crystal oscillator, or a piezo-ceramic element.

The magnetic sensor 250 is a sensor that detects the magnitude and direction of the ambient magnetic field. The magnetic sensor 250 is, for example, worn by the user or attached to the clothes, and detects the Earth's magnetic field (the magnetic field of the Earth) to consequently detect a orientation. The magnetic sensor 250 provides information indicating the detected orientation (hereinafter referred to as "orientation information") to the processing device 100. The magnetic sensor 250, for example, includes a Hall element, a magnet resistive element, or a magnetic impedance element.

The buzzer 300 generates an alarm in accordance with the control of the processing device 100. This alarm is a sound informing the user of a possibility that the user may suffer heatstroke, when the estimated deep body temperature is above a predetermined threshold or when the estimated deep body temperature increases (for example, 1.5° C. or more) above the predetermined value. The buzzer 300 includes an electromagnet and a diaphragm to generate a sound according to the electrical signal provided by the processing device 100. The function of alarming means is realized, for example, cooperatively by the processing device 100 and the buzzer 300.

The terminal device 400 is a device that serves as a user interface of the processing device 100. The terminal device 400, for example, generates an alarm in the form of sound, or using a screen display in accordance with control by the processing device 100. The terminal device 400, for example, includes a non-illustrated CPU, ROM, RAM, flash memory, and communication interface. Examples of the terminal device 400 include a smartphone, a tablet terminal, a smart watch, a head mounted display.

Figure 3:
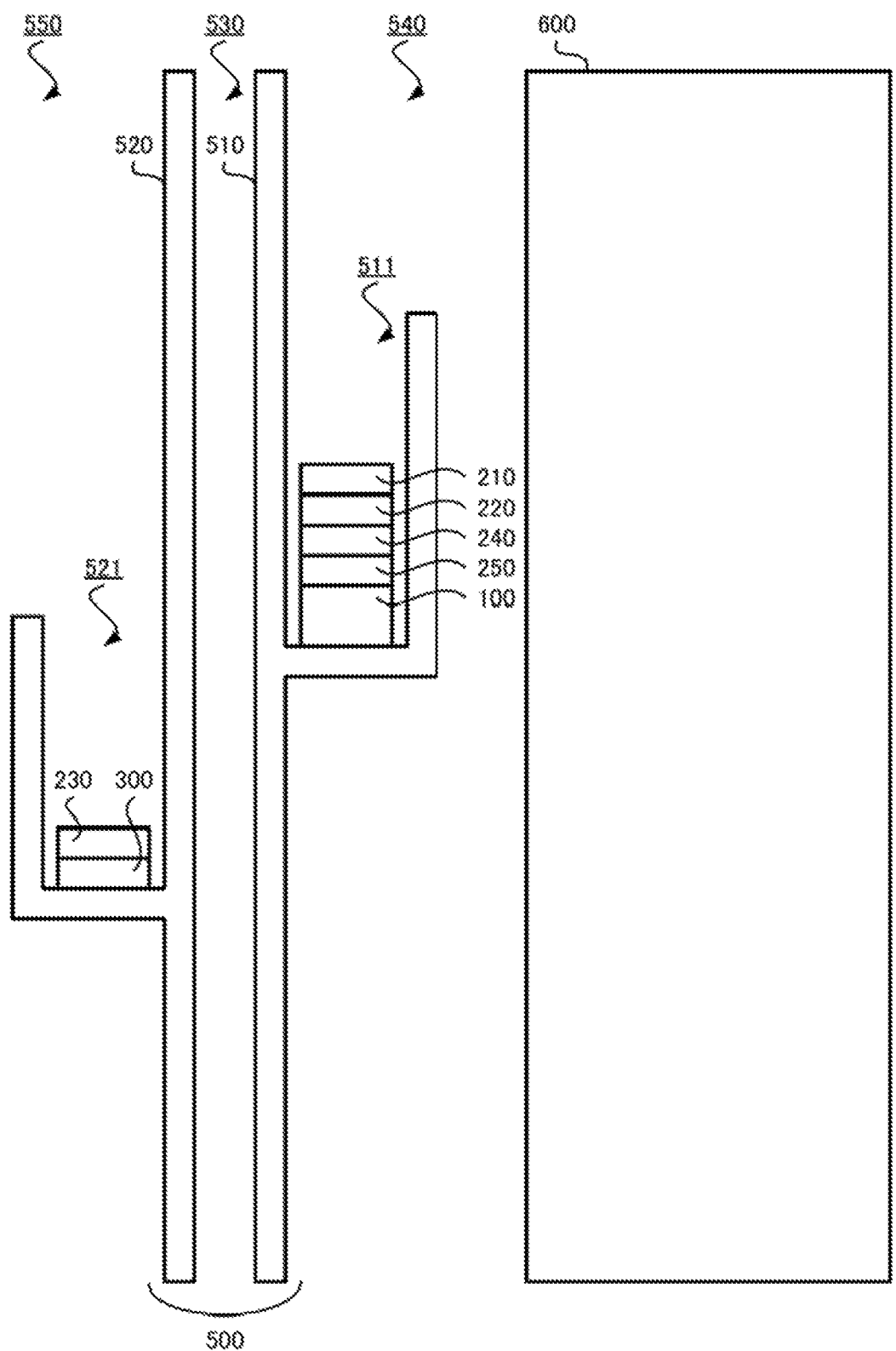
FIG. 3 is a diagram illustrating storage locations for modules.

Next, an arrangement example of the processing device 100, the sensors, and the buzzer 300 is described with reference to FIG. 3. FIG. 3 is a diagram illustrating the state in which the processing device 100, the sensor, and the buzzer 300 are attached to the clothes 500. FIG. 3 illustrates an example in which the clothes 500 include a lining 510 and a shell 520 with a space 530 formed therebetween. With the space 530 provided to the clothes 500, insulation between a space 540 that is a space inside the clothes 500 (the space between the clothes 500 and an under garment 600 worn by the user) and a space 550 that is a space outside the clothes 500 improves. In addition, the shell 520 is made of a material that is highly insulating.

The lining 510 is provided with an inner pocket 511, and the shell 520 is provided with an outer pocket 521. The processing device 100 and the buzzer 300 each are housed, for example, in either one of the inner pocket 511 or the outer pocket 521. In addition, the sensors each are housed in either one of the inner pocket 511 or the outer pocket 512. The temperature sensor 210 is housed in the inner pocket 511 for measuring the temperature inside the clothes. The air pressure sensor 230 is housed in the outer pocket 521 because the air pressure outside the clothes 500 is preferably measured inside the clothes 500 with the air pressure sensor 230. The buzzer 300 is housed in the outer pocket 521 so that an alarm is easily transmitted to the user.

The processing device 100, the acceleration sensor 220, the angular rate sensor 240, and the magnetic sensor 250 each may be housed in either one of the inner pocket 511 or the outer pocket 521. Note that the acceleration axis to be detected with the acceleration sensor 220 and the angular rate axis to be detected by the angular rate sensor 240 are determined based on the direction detected by the magnetic sensor 250. For this reason, the acceleration sensor 220, the angular rate sensor 240, and the magnetic sensor 250 are fixed to one another so that the positional relationships among the sensors do not changed. In the present embodiment, the processing device 100, the temperature sensor 210, the acceleration sensor 220, the angular rate sensor 240, and the magnetic sensor 250 are fixed to one another so that the positional relationships among the sensors do not change.

Next, the mathematical model used to estimate the deep body temperature is described with reference to FIG. 4. The mathematical model is expressed by a simultaneous differential equation composed by six equations that includes the below-described Equation (1) to Equation (6). The first equation, for example, corresponds to Equation (1). The second equation, for example, corresponds to Equation (2). The third equation, for example, corresponds to Equation (3). The fourth equation, for example, corresponds to Equation (4). The fifth equation, for example, corresponds to Equation (5). The sixth equation, for example, corresponds to Equation (6).

$$dQ1/dt = F0 - F1 \quad \text{Equation (1)}$$

$$dQ2/dt = F1 - F2 \quad \text{Equation (2)}$$

$$F1 = (T1 - T2)/R1 \quad \text{Equation (3)}$$

$$F2 = (T2 - T3)/R2 \quad \text{Equation (4)}$$

$$T1 = Q2/C1 \quad \text{Equation (5)}$$

$$T2 = Q2/C2 \quad \text{Equation (6)}$$

Equation (1) is an equation in which an amount of change in a first heat amount is expressed by a difference between heat production amount and a first heat flow amount. The first heat amount is a heat amount of muscles of the user. The first heat flow is a heat flow amount supplied from the muscles of the user to the blood of the user. Q1 is the first heat amount, and dQ1/dt indicates the amount of change in the first heat amount per unit time. The "unit time" is, for example, one minute, ten seconds, or one second. The "unit time" hereinafter means one minute. F0 is a heat production amount. The heat production amount is described later. F1 is the first heat flow amount. In Equation (1), the amount of change in the heat amount of the muscles is defined by the difference between the heat production amount that is the heat flow amount going into the muscles and the heat flow amount going out of the blood.

Equation (2) is equation in which an amount of change in the second heat amount is expressed by the difference between the first heat flow amount and the second heat flow amount. The second heat amount is a heat amount of the blood of the user. The second heat flow amount is a heat flow amount supplied from the blood of the user to the inside of the clothes 500. Q2 is the second heat amount and dQ2/dt is the amount of change in the second heat amount per unit time. F2 is the second heat flow amount. Equation (2) indicates that the amount of change in the heat amount of the blood is defined by the difference between the heat flow amount going into the blood from the muscles, and the heat flow amount going out of the blood to the inside of the clothes 500.

Equation (3) is equation in which the first heat flow amount is expressed by the ratio of the difference between the amount of change in the first temperature and the amount of change in the second temperature to the first thermal resistance value. The first thermal resistance value is the user muscles to user blood thermal resistance value, and is a value indicating the difficulty of heat transfer from the muscles to the blood. The first temperature is the temperature of the muscles of the user. The second temperature is the temperature of the blood of the user. R1 is a first thermal resistance value, T1 is the amount of change in the first temperature per unit time. T2 is the amount of change in the second temperature per unit time. Equation (3) indicates that the heat flow amount flowing from the muscles to the blood is defined by a ratio of the difference between the amount of chain in the temperature of the muscles and the amount of change in the temperature of the blood to the difficulty of heat transfer from the muscles to the blood.

Equation (4) is an equation indicating the second heat flow amount by the ratio of the difference between the amount of change in the second temperature and the amount of change in the temperature inside clothes to the second thermal resistance value. The second thermal resistance value is the thermal resistance value from the blood of the user to the clothes 500, and a value indicating the difficulty of heat transfer from the blood to the clothes. R2 is a second thermal resistance value. T3 is the amount of change in the temperature inside clothes per unit time. Equation (4) indicates that the heat flow amount flowing from the muscles to the blood is defined by a ratio of the difference between the amount of change in the temperature of the muscles to the amount of change in the temperature of the blood to the difficulty of the temperature transmission from the muscles to the blood.

Equation (5) is an equation indicating the amount of change in the first temperature by the ratio of the first heat amount to the first heat capacity. The first heat capacity is the heat capacity of the muscles of the user. C1 is the first heat capacity. Equation (5) indicates that the temperature change of the muscles is defined by the ratio of the heat capacity of the muscles to the heat amount of the muscles.

Equation (6) is equation in which the amount of change in the second temperature is indicated by the ratio of the second heat amount to the second heat capacity. The second heat capacity is the heat capacity of the blood of the user. C2 is the second heat capacity. Equation (6) indicates that the temperature change of the blood is defined by the ratio of the heat capacity of the blood to the heat amount of the blood.

Figure 4:
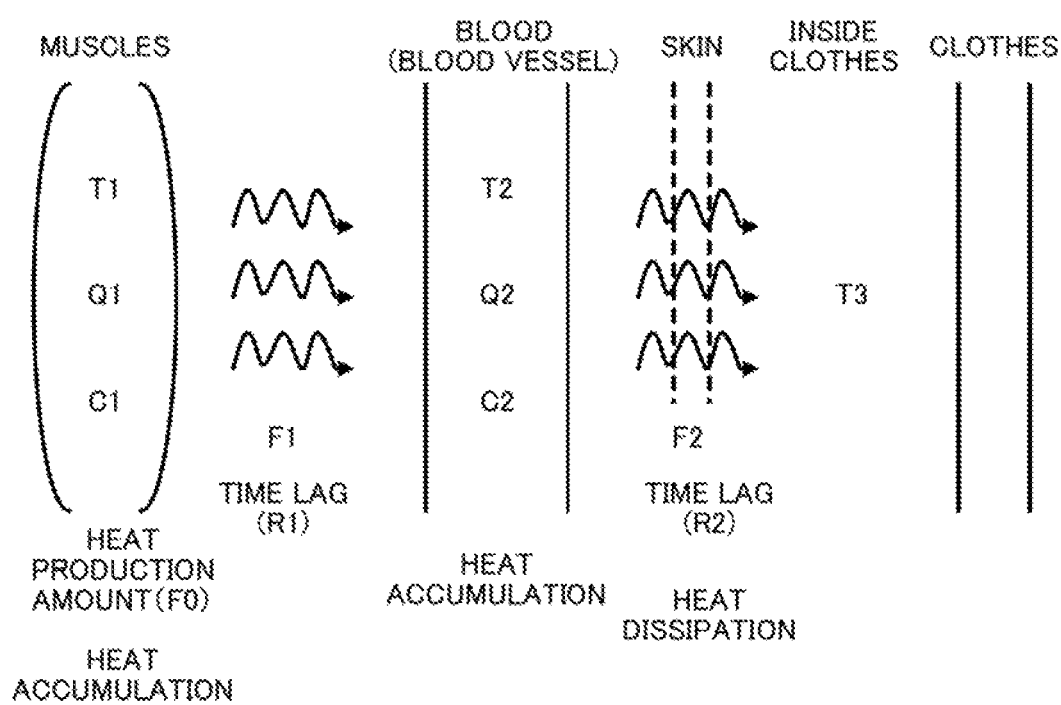
FIG. 4 is an explanatory diagram of a mathematical model.

FIG. 4 illustrates the state in which, upon generation of heat of the heat production amount (F0) in the muscles, heat of the first heat flow amount (F1) flows from the muscles toward the blood at a rate depending on the first thermal resistance value (R1), and then heat of the second heat flow amount (F2) flows from the blood toward the inside of the clothes 500 at a rate depending of the second thermal resistance value (R2). Here, the second temperature is estimated based on the heat production amount and the temperature inside the clothes, while the second temperature is estimated as the deep body temperature. That is, in the present embodiment, the second temperature that is a temperature of the blood of the user is considered to be the deep body temperature of the user.

In the present embodiment, F0 is calculated based on the acceleration information and the air pressure information; T3 is calculated based on the temperature information; R1, R2, C1, and C2 are fixed values, Q1, Q2, F1-F2, T1, and T2 are variables. The above fixed value is determined, for example, by the value obtained when the correlation coefficient is closest to "1", where the correlation coefficient is calculated between the calculated value waveform indicating a time change in the calculated value of the deep body temperature and the actual measured waveform indicating the time change in the actual measurement value of the deep body temperature. Alternatively, this fixed value can be calculated by a correlation equation between a value obtained when the correlation coefficient is the closest to "1", and a value based on the physical features of the user such as a value based on weight and the like of the user.

Here, a technique for calculating the heat production amount is described. The heat production amount can basically be calculated based on the acceleration of the user during physical exercise. Note that the heat production amount can be expected to be calculated with more accuracy if the amount of movement of the user in a height direction is taken into account, in addition to the acceleration of the user. Thus, in the present embodiment, a technique for calculating the heat production amount based on the acceleration of the user and the amount of movement of the user in the height direction is described. Here, the technique is summarized for the description thereof because Japanese Patent Application No. 2008-220517 includes the detailed description of this technique. The heat production amount is calculated, for example, by, the four equations including the following Equation (7) to Equation (10).

$$VM = \Sigma \sqrt{(x^2 + y^2 + z^2)} \qquad \text{Equation (7)}$$

$$VO2 = 0.044 \times VM + 1.365 \times Hu + 0.553 \times Hd \qquad \text{Equation (8)}$$

$$EE = VO_2 \times 4825 \times BW/1000 \qquad \text{Equation (9)}$$

$$F0 = EE \times 0.8 \qquad \text{Equation (10)}$$

In Equation (7), "VM" indicates the magnitude of the acceleration of the user. Strictly speaking, "VM" indicates the magnitude of the cumulative acceleration that is a value of the acceleration applied to the user over a period of the unit time. "VM" is expressed in units of mG. "x" is an instantaneous value for acceleration in the x-axis direction. "y" is an instantaneous value for the acceleration in the direction. "z" is the instantaneous value for the acceleration in the z-axis direction. "VM" is calculated based on the acceleration information that is provided from the acceleration sensor 220 to the processing device 100. More specifically, VM is calculated by the accumulation, over a period of the unit time, of the instantaneous value of the acceleration, as represented by acceleration information acquired in predetermined sampling periods such as 0.1 seconds. Hereinafter, a sampling cycle is taken to be 0.1 seconds. Note that gravitational acceleration is considered to not affect an oxygen consumption amount or the heat production amount. Thus, the instantaneous value of the above-described acceleration is considered as a value that excludes gravitational acceleration. For example, when the z-axis direction is the vertical direction, the value calculated by subtracting the gravitational acceleration from the instantaneous value of acceleration in the z-axis direction is used as "z" in Equation (7).

In Equation (8), "VO$_2$" is an oxygen consumption amount per unit time per unit body weight, such as per 1 kg. "VO$_2$ is expressed in units of" mL/kg/min. "Hu" is an accumulated degree of the rise per unit time. "Hd" is an accumulated degree of the drop per unit time. "Hu" and "Hd" are expressed in units of m/min. "Hu" and "Hd" can be calculated based on the amount of change in the air pressure indicated by the air pressure information that is acquired every predetermined sampling cycle. Note that when the user moves in the height direction, a change in the air pressure is used. That is, when the user moves in the upward direction, the air pressure drops, and when the user moves in the downward direction, the air pressure rises.

In Equation (9), "EE" indicates a total energy expenditure amount. "EE" is expressed in units of kcal/min. 4.825 is a predetermined constant and is expressed in units of kcal/L. "BW" is a weight. "BW" is expressed in units of kg. 1000 is a predetermined constant, and the unit thereof is mL/L.

In Equation (10), "F0" is a heat production amount per unit time. "F0" is expressed in units of kcal/min. "0.8" is a predetermined constant. 0.8 indicates that, of the total energy expenditure amount, 20% is expended due to exercise, and 80% is changed into heat.

As described above, the heat production amount of the user can be calculated based on the acceleration that is applied to the user and the amount of movement of the user in the vertical direction. That is, the heat production amount of the user can be calculated based on the acceleration information and the air pressure information. Note that when the amount of movement of the user in the vertical direction is small, the heat production amount of the user can be calculated based on the acceleration applied to the user without the air pressure information.

In addition, the calculation accuracy of the heat production amount of the user can be improved by identifying the exact movement of the user based on the angular rate information provided by the angular rate sensor 240. In addition, the calculation accuracy of the heat production amount of the user can be improved by identifying the exact movement of the user based on the direction information provided by the magnetic sensor 250.

Figure 5:
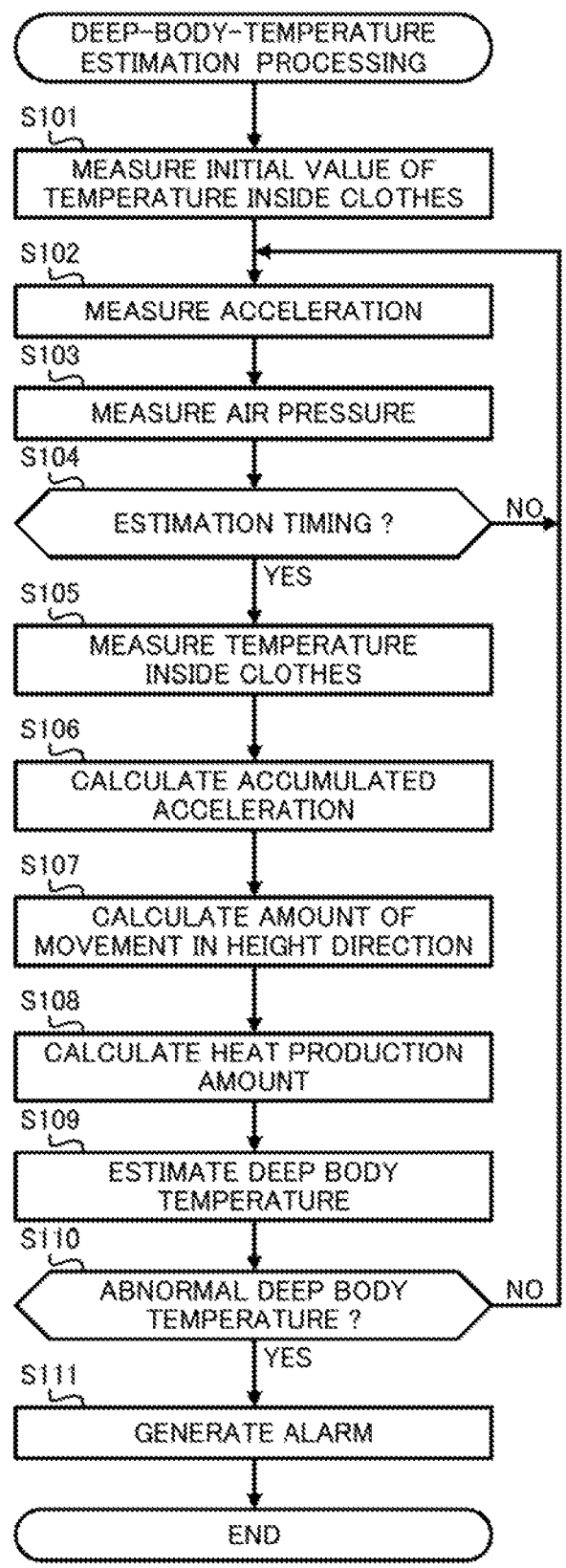
FIG. 5 is a flowchart indicating deep-body-temperature estimation processing performed by the processing device according to an embodiment of the present disclosure.

Next, a deep-body-temperature estimation processing performed by the processing device 100 according to the present embodiment is described with reference to FIG. 5. The deep-body-temperature estimation processing is, for example, performed in response to processing device 100 being powered on.

First, the CPU 11 measures the initial value of the temperature inside the clothe (step S101). For example, the CPU 11 acquires the temperature information from the temperature, sensor 210 to store the acquired temperature information in the flash memory 14 as information indicating the initial value of the temperature inside clothes.

Upon completion of the processing of step S101, the CPU 11 measures the acceleration (step S102). For example, the CPU 11 acquires the acceleration information from the acceleration sensor 220 and stores the acquired acceleration information in the flash memory 14.

Upon the completion of the processing in step S102, the CPU 11 measures the air pressure (step S103). For example, the CPU 11 acquires the air pressure information from the air pressure sensor 230 and stores the acquired air pressure information in the flash memory 14.

Upon the completion of the processing in the step S103, the CPU 11 determines whether the time is the deep-body-temperature estimation timing (step S104). The deep-body-temperature estimation timing is a timing that occurs every unit of time, that is, a timing that occurs every one minute, for example. The CPU 11 determines whether the time is the deep-body-temperature estimation timing based on information provided by the RTC 15. Upon determination that the time is not the deep-body-temperature estimation timing (NO in step S104), processing by the CPU 11 returns to step S102. Note that the processing of step S102 and the processing of step S103 occur each sampling period, for example, every 0.1 seconds.

Upon determination that the time is the deep-body-temperature estimation timing (YES in step S104), the CPU 11 measures the temperature inside the clothes (step S105). For example, the CPU 11 acquires the temperature information from the temperature sensor 210 and stores the acquired temperature information in the flash memory 14 as information indicating the temperature inside the clothes.

Upon completion of the processing in step S105, the CPU 11 calculates the accumulated acceleration (step S106). For example, the CPU 11 calculates the accumulated acceleration from the acceleration measured in step S102 by using Equation (7).

Upon completion of the processing in step S106, the CPU 11 calculates the amount of movement in the height direction (Step S107). For example, the CPU 11 calculates the amount of movement in the height direction based on the air pressure calculated in Step S103. The amount of movement in the vertical direction includes the accumulated degree of the rise and the accumulated degree of the drop.

Upon the completion of the processing in Step S107, the CPU 11 calculates the heat production amount (Step S108). For example, the CPU 11 calculates the heat production amount using the accumulated acceleration calculated in the step S106, Equation (8), Equation (9), and Equation (10).

Upon the completion of the processing in Step S108, the CPU 11 estimates the deep body temperature (step S109). For example, the CPU 11 estimates the deep body temperature using the temperature inside the clothes measured in step S105, the heat production amount calculated in Step S108, and the simultaneous differential equations of Equation (1) to Equation (6). Although is the amount calculated from the simultaneous differential equation is the amount of change in deep body temperature, the deep body temperature can be calculated by adding the amount of change in the deep body temperature to a predetermined reference value of the deep body temperature, such as 37° C. Note that, the estimation of the deep body temperature has basically the same meaning as the estimation of the amount of change in the deep body temperature.

Upon completion of the processing in step S109, the CPU 11 determined as to whether the deep body temperature is abnormal (step S110). For example, the CPU 11 determined that the deep body temperature is abnormal when the deep body temperature exceeds the threshold (for example, 39° C.) or when the deep body temperature was increased above the predetermined value (for example 1.5° C.). Upon determining that the deep body temperature is not abnormal (NO in step S110), the CPU 11 returned the processing back to step S102.

Alternatively, upon determination that the deep body temperature is abnormal (YES in step S110), the CPU 11 generates the alarm (step S111). For example, the CPU 11 output a sound corresponding to the alarm from the buzzer 300. Upon the completion of the processing of step S111, the CPU 11 terminates the deep-body-temperature estimation processing.

In the present embodiment, the deep body temperature is estimated based on the temperature inside the clothes and the heat production amount by using the simultaneous differential equation indicating the correspondence relationship between the temperature inside the clothes that is the temperature inside the clothes of the user and the heat production amount that is the heat amount produced inside the body of the user. Therefore, the present embodiment can estimate the deep body temperature of the user with high accuracy.

Furthermore, the present embodiment can estimate the deep body temperature with high accuracy. For this reason, the estimated deep body temperature can also be used as the index indicating danger of heat stress such as heatstroke that the human body feels.

In addition, the present embodiment performs the estimation by regarding the blood temperature of the user as the deep body temperature of the user. Here, the blood temperature is considered to be a temperature that is closer to the deep body temperature than a temperature such as the rectum temperature. Thus, the present embodiment can estimate the deep body temperature of the user with high accuracy. Furthermore, in the present embodiment, the temperature of the object to be measured is the temperature inside the clothes. Therefore, such measurement of the temperature is easier in comparison to the case where the rectum temperature is measured.

In the present embodiment, the mathematical model defined by the simultaneous differential equation including six equations is described that assumes that the deep body temperature can be calculated with high accuracy based on the heat production amount and the temperature inside clothes. Hereinafter, Example 1 to Example 3 describe a investigation result of the validity of this mathematical model, and a method of determining parameters used in this mathematical model.

Example 1

First, conditions occurring in Example 1 are described. In Example 1, a deep-body-temperature probe measurement device (not illustrated) that performed actual measurement of an esophagus temperature as the deep body temperature, the temperature sensor 210 for measuring the temperature inside the clothes, the acceleration sensor 220, the air pressure sensor 230, the angular rate sensor 240, and the magnetic sensor 250 were attached to a subject who wore the clothes 500. In addition, a capsule type sweat-amount measuring device, a mask type oxygen-intake measuring device or the like were used. Six subjects were used, and the subjects were designated as "S", "H", "M", "Y", "K", and "U". The deep-body-temperature probe measurement device was attached to the esophagus of the subject. The temperature sensor 210, the acceleration sensor 220, the angular rate sensor 240, and the magnetic sensor 250 were disposed inside the inner pocket 511 that was included in the clothes 500. The air pressure sensor 230 was disposed inside the outer pocket 521 that was included in the clothes 500.

The clothes 500 worn by the subject were clothes as described in Comparative Example 4 of Unexamined Japanese Patent Application Kokai Publication No. 2014-091307. The clothes 500 were made of a multi-layer fabric and obtained by stitching the fabric into the shape of protective suits for firefighting (fire-proof suits). Specifically, for an outmost layer, a fabric having a plain weave ripstop structure was manufactured using spun yarns (40/2 count). The spun yarns were formed of beat-resistant fibers in which polymetaphenylene isophthalamide fibers (CONEX (trademark) manufactured by Teijin Limited) and co-poly-(paraphenylene/3,4'-oxydiphenylene terephthalamide) fibers (TECHNORA (trademark) manufactured by Teijin Limited) were mixed in a ratio of 90:10. The fabric weight of the outer surface layer was 380 g/m².

For the intermediate layer, a woven fabric (fabric weight: 80 g/m²) having a plain weave structure was manufactured using spun yarns (40/-count) and a polytetrafluoroethylene-moisture permeable and waterproof film (manufactured by Japan Gore-Tex Co., Ltd.) was applied to the woven fabric. The spun yarns were formed of heat-resistant fibers in which polymetaphenylene isophthalamide fibers (CONEX, registered trademark, manufactured by Teijin Limited) and co-poly-(paraphenylene/3,4'-oxydiphenylene terephthalamide) fibers (TECHNORA, registered trademark, manufactured by Teijin Limited) were mixed in a ratio of 95.5. For the heat shielding layer (inner layer), a woven fabric having a plain weave structure was manufactured using filaments having a total fineness of 1670 dtex that were formed of co-poly-(paraphenylene/3,4'-oxydiphenylene terephthalamide) fiber yarns (TECHNORA, registered trademark, manufactured by Teijin Limited). The fabric weight of the heat shielding layer was 210 g/m².

The inclination angle of the treadmill on which the subject walked was set to 5% and the operational rate of the treadmill was speeded up in a stepwise manner. In particular, the operational rate of the elapsed period from the minute 0 to the minute 3 was set to 0 km/h for three minutes after the start of the measurement, the operational rate of the elapsed period from the minute 3 to the minute 12 was set to 1.5 km/h for nine minutes, the operational rate of the elapsed period from the minute 12 to the minute 21 was set to 3.0 km/h for nine minutes, the operational rate of the elapsed period from minute 21 to the minute 30 was set to 4.5 km/h for nine minutes, and the operational rate of the elapsed period after the minute 30 was set to 6.0 km/h. Note that for safety the evaluation was terminated at the point of time when the heart rate reached 180 or more, or the esophagus temperature reached 38.5° C.

FIG. 6 indicates master data of the subjects. The master data includes age, sex, height (cm), weight (kg), BMI, body surface area (cm²), measurement time, (min), weight after exercise (kg), and weight difference (kg). The BMI is indicated as weight/height². The body surface area is indicated as weight$^{0.444}$×height$^{0.663}$×88.83/10000. The weight difference is a value obtained by subtracting the weight after exercise from the weight (weight before exercise).

Figure 8:
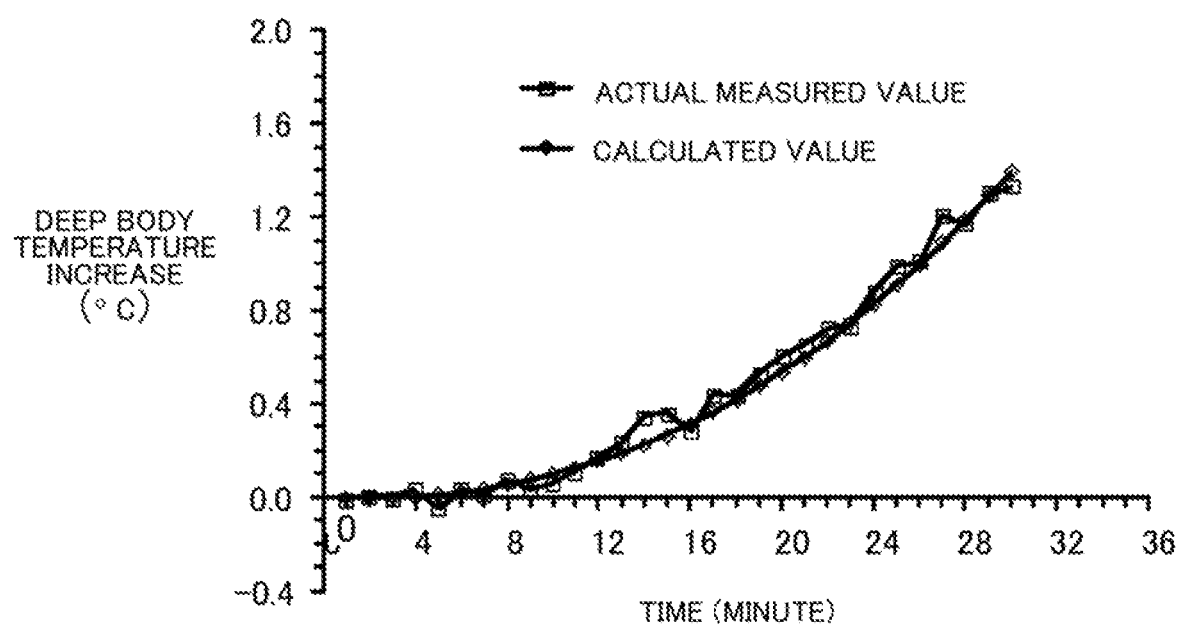
FIG. 8 is a diagram of a relationship between actual measured values and calculated values.

The heat production amount was calculated by the technique described in the present embodiments. Note that techniques disclosed in Unexamined Japanese Patent Application Kokai Publication No. 2008-220517 and Japanese Patent Application No. 3571272 may be used for the heat production amount. The temperature inside the clothes was the temperature measured by the temperature sensor 210. FIG. 7 indicates the result data of Example 1. FIG. 8 indicates a relationship between actual measured values and calculated values. Note that Example 1 is an example listing every calculated parameter separately. The parameters refer to the four parameters C1, C2, R1, and R2 in the simultaneous differential equation that includes six equations from Equation (1) to Equation (6).

As illustrated in FIG. 8, the actual measured value of the deep body temperature increases with the passage of time. For ease of the description, the deep body temperature is indicated as the amount of change in temperature, that is, increasing degree of the deep body temperature, with reference to the deep body temperature at the start of the measurement. Here, when the mathematical model expressed by the above-described simultaneous differential equation is appropriate, the difference is expected to be small between the change, over time, in the deep body temperature calculated by using the mathematical model and the change, over time, in the deep body temperature actually measured. That is, the correlation coefficient between calculated value waveform indicating a change in the calculated value of the deep body temperature over time, and actual measured value waveform indicating a change in the actual measured value of the deep body temperature, is expected to be close to 1. Then, the calculated value was a waveform that was obtained by finding the calculated value of the deep body temperature for each of the subjects while changing C1, C2, R1, and R2. Then, the parameters (C1, C2, R1, R2) are identified for when the correlation coefficient between the calculated value waveform and actual measured waveform is the closest to 1. FIG. 7 indicates the parameters (C1, C2, R1, R2) from which the maximum correlation coefficient is obtained for each of the subjects.

Note that the correlation coefficient falling in a range of 1 to 0.7 means a strong positive correlation. The correlation coefficient falling in a range of 0.7 to 0.4 means an approximately intermediate positive correlation. The correlation coefficient falling in a range of 0.4 to 0.2 means a weak positive correlation. The correlation coefficient falling in a range of 0.2 to −0.2 means hardly any correlation. The correlation coefficient falling in a range of −0.2 to −0.4 means a weak negative correlation. The correlation coefficient falling in a range of −0.4 to −0.7 means an approximately intermediate negative correlation. The correlation coefficient falling in a range of −0.7 to −1 means a strong negative correlation.

"SLOPE" is the slope of the approximation straight line obtained by the plotted points when the amount of change in deep body temperature per minute is plotted with the actual measured value indicated by the vertical axis, and the calculated value indicated by the horizontal axis. Note that this straight line can be obtained by a least squares method. The "Intercept" is an intercept of this straight line, for example. "AVG" indicates an average value. "SD" indicates a standard deviation, that is the variance. "SE" indicates the standard error, that is an estimation error of the estimated amount.

As indicated in FIG. 7, when C1, C2, R1, and R2 are adjusted for each of the subjects, the correlation coefficients for all of the subjects are roughly 0.97 or more. That its, according to Example 1, the above-described mathematical model is believed to be plausible.

Example 2

In Example 2, the generalization of the parameters is attempted in light of the result data of Example 1. Specifically, Example 2 uses the average value of the parameters of each of the subjects obtained in Example 1. FIG. 9 indicates the result data of Example 2.

As indicated in FIG. 9 when the average value is applied to every parameter (C1, C2, R1, R2), the correlation coefficients for all of the subjects are roughly 0.97 or more. That is, according to Example 2, the above-described mathematical model is believed to be established even though predetermined values, that is, average values, are applied to all of the parameters (C1, C2, R1, R2) in the above-described mathematical model.

Example 3

Example 3 investigated as to whether there is a correlation between the parameters and the weights of the users, in light of the result data of the Example 1. Specifically, Example 3 first investigated as to whether a correlation between all of the parameters (C1, C2, R1, R2) and the weight is found. FIG. 10 indicates the result data 1 of Example 3.

Figure 11:
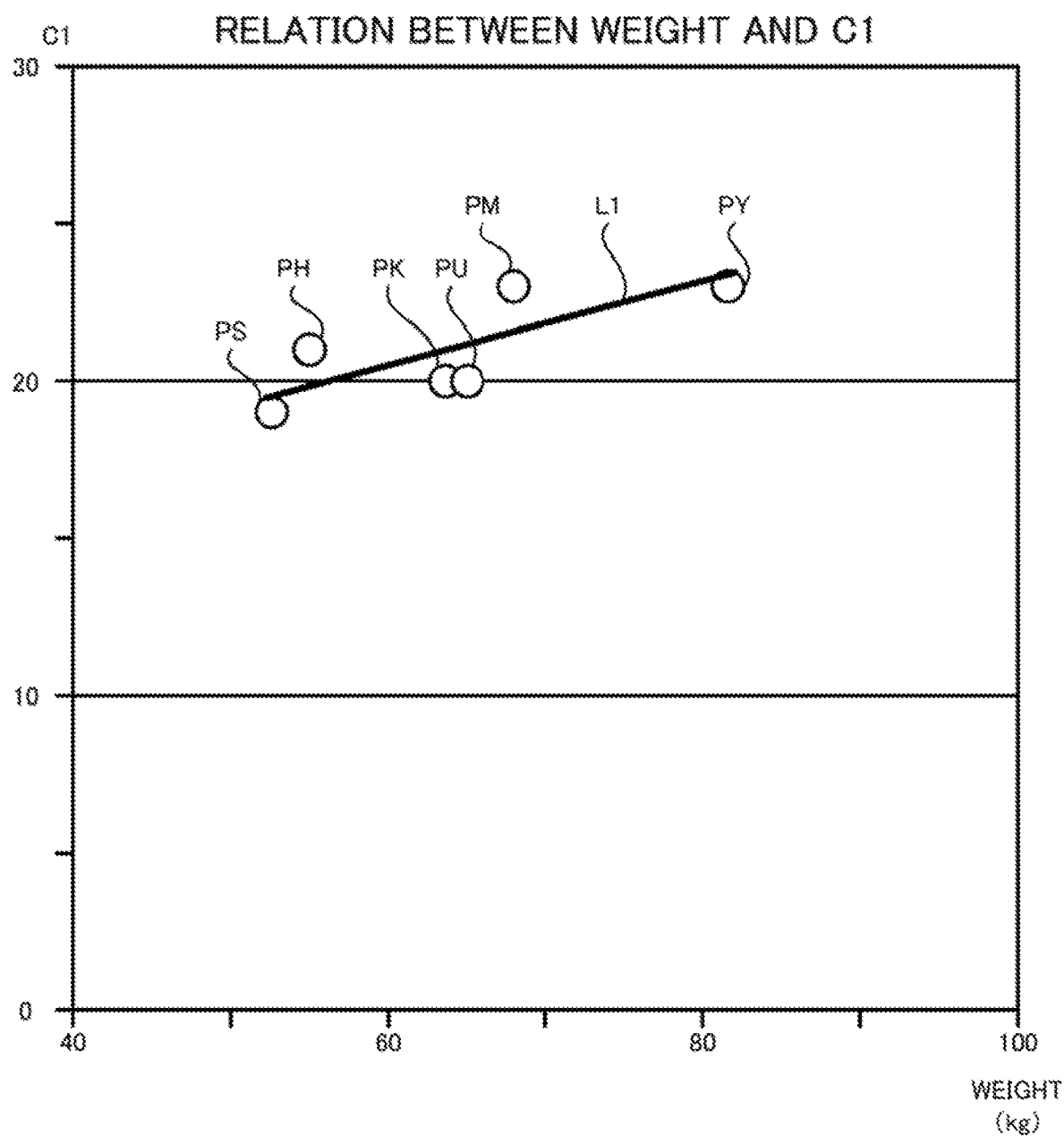
FIG. 11 is a diagram of a relationship between a weight and C1.

The correlation coefficient in FIG. 10 is the correlation coefficient between each of the parameters and the weight. The technique for calculating the correlation coefficient between each of the parameters and the weight is described with reference to FIG. 11. FIG. 11 is a diagram indicating the relation between the weight and C1, and is a scatter diagram of each of the subjects with the weight being indicated along the horizontal axis and C1 being indicated along the vertical axis. FIG. 11 indicates a point "PS" identified by the weight of the subject indicated by "S" (hereinafter referred to as simply "S", other subjects being similarly denoted) and the adjusted C1 of S in Example 1. "PH" indicates a point that is identified by the weight of H and adjusted C1 of H. "PM" indicates a point that is identified by the weight of M and adjusted C1 of M. "PY" indicates a point that is identified by the weight of Y and adjusted C1 of Y. "PK" indicates a point that is identified by the weight of K and adjusted C1 of K. "PU" indicates a point that is identified by the weight of U and adjusted C1 of U.

Here, "r" that is the correlation coefficient between the weight and C1 was the correlation coefficient between the weight waveform when all of the subjects is arranged in order of weight and the C1 waveform when all of the subjects are arranged in order of C1. Here, r=0.754, and $r^2$=0.568 were obtained. Since the correlation coefficient between the weight and C1 is 0.754, the positive correlation between the weight and C1 is considered to be strong. That is, specifying C1 by using the weight as an index is considered to be effective. Thus, attempts are made to identify the correspondence relation between the weight and C1. First, a line L1 indicates a straight line that approximates PS, PH, PM, PY, PK, and PU. L1 is identified by, for example, the least square method. Here, taking the weight to be "BW", C1=0.1234×BW+13.062 is obtained.

The relations between the weight and C2, the weight and R1, and the weight and R2 could be investigated by calculating the correlation coefficients thereof in the same manner as the relation between the weight and C1. Due to the correlation coefficient between the weight and C2 of 0.555, a certain degree of the positive correlation between the weight and C2 is considered to be obtained. Thus, when the correspondence relation between the weight and C2 is calculated, C2=0.0887×BW+15.963 is obtained. In contrast, since the correlation coefficient between the weight and R1 is 0.356, less correlation is considered to exist between the weight and R1. Similarly, since the correlation coefficient between the weight and R2 is 0.039, less correlation is considered to exist between the weight and R2.

Thus, in Example 3, C1 and C2 are calculated by the correlation equation using the weight, while the average values were used for R1 and R2. FIG. 12 indicates the result data 2 of Example 3. As indicated in FIG. 12, when C1 and C2 are identified by using the weight and the average values used for R1 and R2, the correlation coefficient of roughly 0.97 or more for all of the subjects is obtained. That is, according to Example 3, the mathematical model is considered to be established even though C1 and C2 are identified by the weight and predetermined values, that is, the average values, for R1 and R2 in the above-described mathematical model.

Example 4

Example 4 investigated as to whether correlation is found between the parameters and the body surface area of the user in light of the result data of Example 1. Specifically, Example 4 investigated as to whether a correlation coefficient is found between all of the parameters (C1, C2, R1, R2) and the body surface area. FIG. 13 indicates the result data 1 of Example 4.

FIG. 13 indicates a correlation coefficient that is the correlation coefficient between the parameters and the body surface area. The technique for calculating the correlation coefficient between the parameters and the body surface area is basically similar to the technique for calculating the correlation coefficient between the parameters and the weight. Regarding C1, an example indicated in FIG. 13 indicates r=0.844, $r^2$=0.712. Since the correlation coefficient between the body surface area and C1 is 0.844, the positive correlation between the body surface area and C1 is considered to be strong. That is, setting C1 using the body surface area as an index is considered effective. Thus, identifying the correspondence relation between the body surface area and C1 is attempted. When the body surface area is indicated as BSA, C1=0.0010×BSA+0.7450 is obtained.

The relation between the body surface area and C2, the relation between the body surface area and R1, and the relation between the body surface area and R2 can be investigated by calculating the correlation coefficient, similarly to the calculation for the relation between the body surface area and C1. Since the correlation coefficient between the body surface area and C2 is 0.680, the relation between the body surface area and C2 is believed to have a certain degree of the positive correlation. Then, when the correspondence relation between the body surface area and C2 is calculated, C2=0.0009×BSA+5.7360 is obtained. In contrast, since the correlation coefficient between the body surface area and R1 is 0.429, the relation between the body surface area and R1 is believed to have less correlation. Similarly, since the correlation coefficient between the body surface area and R2 is 0.125, the relation between the body surface area and R2 has is considered to be less correlated.

Thus, in Example 4, C1 and C2 are calculated by the equation using BSA, while the average value is used for R1 and R2. FIG. 14 indicates the result data 2 of Example 4. As indicated in FIG. 14, when C1 and C2 are identified by using BSA, and average values are used for R1 and R2, the correlation coefficients for all of the subject are roughly 0.97 or more. That is, according to Example 4, even when, in the above-described mathematical model, C1 and C2 are identified by using BSA while a predetermined value, that is, average values, are used for R1 and R2, the mathematical model is considered to be established.

Example 5

In Example 5, in light of the result data of Example 3 and Example 4, C1 is specified by the weight, and C2 is specified by the body surface area, and average value is used for R1 and R2. That is, in Example 5, C1=0.1234×BW+13.062, C2=0.0009×BSA+5.7360, R1=2.4, and R2=24.2 are used. FIG. 15 indicates the result data of Example 5.

In FIG. 15, the value T is a statistical testing amount. The value T is expressed by $T=r\times(\sqrt{(N-2)})/(\sqrt{1-r^2})$. Note that "N" is the number of data. In addition, a P value is for a two tailed probability of the T distribution. As indicated in FIG. 15, when C1 is specified by using "BW", C2 is specified by using "BSA", and an average value is used for R1 and R2, the correlation coefficients for all of the subjects are roughly 0.97 or more. That is, according to Example 5, in the above-mentioned mathematical model, even though C1 is specified by using BW, C2 is specified by using BSA, and a predetermined value (that is, an average value) is used for R1 and R2, the mathematical model is considered to be established.

FIG. 16 indicates the final result data based on Example 1 to Example 5. FIG. 16 indicates the correlation coefficient, slope, and intercept for four conditions. The four requirements included the first condition in which C1 is specified by using the weight while C2 is specified by using the body surface area, the second condition in which C1 is specified by using the weight while C2 is specified by using the average value, the third condition in which C1 and C2 are specified by using the weight, and the fourth condition in which C1 and C2 are specified by the body surface area. Note that, for each of the conditions, the predetermined values (that is, average values) are used for R1 and R2. In addition, the first condition corresponded to Example 5, the third condition corresponded to Example 3, and the fourth condition corresponded to Example 4.

As indicated in FIG. 16, when C1 and C2 are identified by the value that is based on the physical characteristics of the user (for example, the weight and the body surface area), and the predetermined value (that is, the average value) is used for R1 and R2, the mathematical model is considered to be established. Note that when the correlation coefficient, SLOPE, and Intercept are taken into account, as the first condition (Example 5), C1 is considered most preferably identified by the weight, C2 is considered most preferably identified by the body surface area, and the predetermined value (that is, the average value) is considered most preferably used for R1 and R2.

Modified Examples

Although embodiments of the present disclosure are described above, embodiments using various types of modification are possible in the implementation of the present disclosure.

In the present disclosure, the parts to use in the configurations, functions, and operations described in the aforementioned embodiments are freely selected. The present disclosure may further use other configurations, functions, and operations in addition to the aforementioned configurations, functions, and operations. Furthermore, the aforementioned embodiments can be freely combined as appropriate. In addition, materials, sizes, electrical characteristics that can be used in the present disclosure are, of course, not limited to the ones indicated in the above examples.

Although the examples of the above temperature inside the clothes include an air temperature between the clothes and the human body, an air temperature between the outer most layer of clothes worn and the clothes that are underneath of the outer most layer of clothes, and the skin temperature of the human body covered by the clothes, the temperature inside the clothes is not limited to such temperatures.

The examples of the physical characteristic of the user include the weight, height, BMI, body fat percentage, perspiration volume, respiration rate, body surface area, and muscle mass, without particular limitation.

The above means of alarm notification notifies when, for example, the above deep body temperature exceeds the predetermined threshold or the increasing degree of the above deep body temperature exceeds the predetermined threshold of degree of increase, but such configuration is not limiting.

In the present embodiment 1, the case is described in which a wide variety of the functions of the processing device 100 are achieved by software (or firmware), that is the functions of the processing device 100 are performed by a program that is executed by the processor. In the present disclosure, such functions may be achieved by hardware. In this case, the processing device 100, for example, includes a processing circuit instead of the CPU 11. Such a processing circuit, for example, includes a single circuit, a composite circuit, a programmed processor, a parallel programmed processor, an application specific integrated circuit (ASIC) a field programmable gate array (FPGA), and combinations thereof.

By use of an operation program for specifying the operation of the processing device 100 according to the present disclosure by an existing personal computer or the information terminal device, the personal computer can be caused to function as the processing device 100 according to the present disclosure. In addition, the method of distribution of such a program is freely selected and for example, the program can be stored in a computer readable recording medium such as a compact disk read-only memory (CD-ROM), digital versatile disk (DVD), memory card, and the like, or distributed via a communication network such as the Internet.

The foregoing describes some example embodiments for explanatory purposes. Although the foregoing discussion has presented specific embodiments, persons skilled in the art will recognize that changes may be made in form and detail without departing from the broader spirit and scope of the invention. Accordingly, the specification and drawings are to be regarded in an illustrative rather than a restrictive sense. This detailed description, therefore, is not to be taken in a limiting sense, and the scope of the invention is defined only by the included claims, along with the full range of equivalents to which such claims are entitled.

This application claims the benefit of Japanese Patent Application No. 2017-147355, filed on Jul. 31, 2017, the entire disclosure of which is incorporated by reference herein.

REFERENCE SIGNS LIST

11 CPU
12 ROM
13 RAM
14 Flash memory
15 RTC
16 Touch screen
17 First communication interface
18 Second communication interface
100 Processing device
210 Temperature sensor
220 Acceleration sensor
230 Air pressure sensor
240 Angular rate sensor
250 Magnetic sensor 300 Buzzer
400 Terminal device
500 Clothes
510 Lining
511 Inner pocket
520 Shell
521 Outer pocket
530, 540, 550 Space
600 Under garments
1000 Deep-body-temperature estimation system

The invention claimed is:

1. A deep-body-temperature estimation system comprising:
   a temperature sensor configured to measure a temperature inside clothes being a temperature inside the clothes worn by a user;
   an acceleration sensor configured to detect an acceleration applied to the user; and
   a hardware processor configured to estimate a heat production amount based on the acceleration detected by the acceleration sensor, the heat production amount being a heat amount generated inside a body of the user, and estimate a deep body temperature based on (i) the temperature inside the clothes measured by the temperature sensor and (ii) the estimated heat production amount, the deep body temperature being a temperature inside the body of the user, wherein
   the hardware processor estimates the deep body temperature by using a mathematical model indicating a correspondence relation among the temperature inside the clothes, the heat production amount, and the deep body temperature,
   the mathematical model is expressed by a simultaneous differential equation comprising:
      a first equation where an amount of change in a first heat amount is expressed by a difference between the heat production amount and a first heat flow amount that is a heat flow amount supplied from muscles of the user to a blood of the user, the amount of change in the first heat amount being a heat amount of the muscles of the user,
      a second equation where an amount of change in a second heat amount is expressed by a difference between the first heat flow amount and a second heat flow amount that is a heat flow amount supplied from the blood of the user to an inside of the clothes, the amount of change in the second heat amount being a heat amount of the blood of the user,
      a third equation where the first heat flow amount is expressed by a ratio of a difference between an amount of change in a first temperature that is a temperature of the muscles of the user and the amount of change in a second temperature that is a temperature of the blood of the user to a first thermal resistance value that is a thermal resistance value from the muscle of the user to the blood of the user,
      a fourth equation wherein the second heat flow amount is expressed by a ratio of a difference between the amount of change of the second temperature and the amount of change in the temperature inside the clothes to a second thermal resistance value that is a thermal resistance value from the blood of the user to the inside of the clothes,
      a fifth equation where the amount of change in the first temperature is expressed by a ratio of the first heat amount to a first heat capacity that is a heat capacity of the muscles of the user, and
      a sixth equation where an amount of change in the second temperature is expressed by a ratio of the second heat amount to a second heat capacity that is a heat capacity of the blood of the user, and
   the hardware processor estimates the second temperature as the deep body temperature.

2. The deep-body-temperature estimation system according to claim 1, wherein
   the first heat capacity and the second heat capacity are values obtained based on physical features of the user, and
   the first thermal resistance value and the second thermal resistance value are predetermined values.

3. The deep-body-temperature estimation system according to claim 2, further comprising:
   an air pressure sensor configured to detect an air pressure around the user, wherein
   the hardware processor estimates the heat production amount based on the acceleration detected by the acceleration sensor and the air pressure detected by the air pressure sensor.

4. The deep-body-temperature estimation system according to claim 1, further comprising:
   an air pressure sensor configured to detect an air pressure around the user, wherein
   the hardware processor estimates the heat production amount based on the acceleration detected by the acceleration sensor and the air pressure detected by the air pressure sensor.

5. The deep-body-temperature estimation system according to claim 1, further comprising:
   an angular rate sensor configured to detect an angular rate applied to the user; and
   a magnetic sensor configured to detect a direction of a magnetic field around the user, wherein
   the acceleration sensor, the angular rate sensor, and the magnetic sensor are fixed to one another, and
   the hardware processor estimates the heat production amount based on the acceleration detected by the acceleration sensor, the angular rate detected by the angular rate sensor, and the direction detected by the magnetic sensor.

6. The deep-body-temperature estimation system according to claim 1, wherein the hardware processor is further configured to provide notification of an abnormality of the user based on the estimated deep body temperature.

7. The deep-body-temperature estimation system according to claim 1, wherein the clothes have a heat shielding effect.

8. The deep-body-temperature estimation system according to claim 7, wherein the heat shielding effect satisfies a requirement in which the HTI 24 that is measured by a method defined in ISO 9151 is three seconds or more.

9. The deep-body-temperature estimation system according to claim 1, wherein the clothes have an air permeability of 1.0 $cm^3/cm^2/s$ or below measured by a method that is defined in JIS L 1096 and that uses a fragile type tester.

10. The deep-body-temperature estimation system according to claim 1, wherein the clothes have a moisture permeability of 1000 $g/m^2/h$ or below measured by a method that is defined in JIS L 1099 and uses a cup method.

11. The deep-body-temperature estimation system according to claim 1, wherein the clothes have a thermal conductivity of 1 kcal/h/m/° C. or below.

12. A heat-stress alarm system comprising:
a temperature sensor configured to measure a temperature inside clothes being a temperature inside the clothes worn by a user;
an acceleration sensor configured to detect an acceleration applied to the user; and
a hardware processor configured to estimate a heat production amount based on the acceleration detected by the acceleration sensor, the heat production amount being a heat amount generated inside a body of the user, estimate a deep body temperature based on (i) the temperature inside the clothes measured by the temperature sensor and (ii) the estimated heat production amount, the deep body temperature being a temperature inside the body of the user, and generate an alarm based on the estimated deep body temperature,
wherein
the hardware processor estimates the deep body temperature by using a mathematical model indicating a correspondence relation among the temperature inside the clothes, the heat production amount, and the deep body temperature,
the mathematical model is expressed by a simultaneous differential equation comprising:
a first equation where an amount of change in a first heat amount is expressed by a difference between the heat production amount and a first heat flow amount that is a heat flow amount supplied from muscles of the user to a blood of the user, the amount of change in the first heat amount being a heat amount of the muscles of the user,
a second equation where an amount of change in a second heat amount is expressed by a difference between the first heat flow amount and a second heat flow amount that is a heat flow amount supplied from the blood of the user to an inside of the clothes, the amount of change in the second heat amount being a heat amount of the blood of the user,
a third equation where the first heat flow amount is expressed by a ratio of a difference between an amount of change in a first temperature that is a temperature of the muscles of the user and the amount of change in a second temperature that is a temperature of the blood of the user to a first thermal resistance value that is a thermal resistance value from the muscle of the user to the blood of the user,
a fourth equation wherein the second heat flow amount is expressed by a ratio of a difference between the amount of change of the second temperature and the amount of change in the temperature inside the clothes to a second thermal resistance value that is a thermal resistance value from the blood of the user to the inside of the clothes,
a fifth equation where the amount of change in the first temperature is expressed by a ratio of the first heat amount to a first heat capacity that is a heat capacity of the muscles of the user, and
a sixth equation where an amount of change in the second temperature is expressed by a ratio of the second heat amount to a second heat capacity that is a heat capacity of the blood of the user, and
the hardware processor estimates the second temperature as the deep body temperature.

13. A deep-body-temperature estimation method comprising:
measuring a temperature inside clothes that is a temperature inside the clothes worn by a user;
detecting acceleration applied to the user;
estimating a heat production amount based on the detected acceleration, the heat production amount being a heat amount generated inside a body of the user; and
estimating a deep body temperature based on the measured temperature inside the clothes and the estimated heat production amount, the deep body temperature being a temperature inside the body of the user,
wherein the estimating the deep body temperature further comprises estimating the deep body temperature by using a mathematical model indicating a correspondence relation among the temperature inside the clothes, the heat production amount, and the deep body temperature,
wherein
the mathematical model is expressed by a simultaneous differential equation comprising:
a first equation where an amount of change in a first heat amount is expressed by a difference between the heat production amount and a first heat flow amount that is a heat flow amount supplied from muscles of the user to a blood of the user, the amount of change in the first heat amount being a heat amount of the muscles of the user,
a second equation where an amount of change in a second heat amount is expressed by a difference between the first heat flow amount and a second heat flow amount that is a heat flow amount supplied from the blood of the user to an inside of the clothes, the amount of change in the second heat amount being a heat amount of the blood of the user,
a third equation where the first heat flow amount is expressed by a ratio of a difference between an amount of change in a first temperature that is a temperature of the muscles of the user and the amount of change in a second temperature that is a temperature of the blood of the user to a first thermal resistance value that is a thermal resistance value from the muscle of the user to the blood of the user,
a fourth equation wherein the second heat flow amount is expressed by a ratio of a difference between the amount of change of the second temperature and the amount of change in the temperature inside the clothes to a second thermal resistance value that is a thermal resistance value from the blood of the user to the inside of the clothes,
a fifth equation where the amount of change in the first temperature is expressed by a ratio of the first heat amount to a first heat capacity that is a heat capacity of the muscles of the user, and
a sixth equation where an amount of change in the second temperature is expressed by a ratio of the second heat amount to a second heat capacity that is a heat capacity of the blood of the user, and
the estimating the deep body temperature further comprises estimating the deep body temperature to be the second temperature.

* * * * *